(12) United States Patent
Wiki

(10) Patent No.: US 8,213,017 B2
(45) Date of Patent: Jul. 3, 2012

(54) ANALYTICAL SYSTEM COMPRISING AN ARRANGEMENT FOR TEMPORALLY VARIABLE SPATIAL LIGHT MODULATION AND DETECTION METHOD EXECUTABLE THEREWITH

(76) Inventor: Max Wiki, Morges (CH)

( * ) Notice: Subject to any disclaimer, the term of this patent is extended or adjusted under 35 U.S.C. 154(b) by 583 days.

(21) Appl. No.: 12/373,972

(22) PCT Filed: Jul. 16, 2007

(86) PCT No.: PCT/IB2007/052831
§ 371 (c)(1),
(2), (4) Date: Sep. 28, 2009

(87) PCT Pub. No.: WO2008/010182
PCT Pub. Date: Jan. 24, 2008

(65) Prior Publication Data
US 2010/0014088 A1     Jan. 21, 2010

(30) Foreign Application Priority Data
Jul. 17, 2006   (CH) ........................................ 1151/06

(51) Int. Cl.
G01N 21/55 (2006.01)
G01B 11/02 (2006.01)
(52) U.S. Cl. .......................... 356/445; 356/447; 356/513
(58) Field of Classification Search .......... 356/445–448, 356/450–458
See application file for complete search history.

(56) References Cited

U.S. PATENT DOCUMENTS

| | | | |
|---|---|---|---|
| 4,683,420 A * | 7/1987 | Goutzoulis | ..................... 324/96 |
| 5,255,075 A | 10/1993 | Cush | |
| 5,445,934 A | 8/1995 | Fodor et al. | |
| 5,598,300 A | 1/1997 | Magnusson et al. | |
| 5,614,990 A * | 3/1997 | Bruce et al. | ..................... 355/71 |
| 6,429,022 B1 | 8/2002 | Kunz et al. | |
| 6,542,241 B1 | 4/2003 | Thorwirth et al. | |
| 6,894,827 B2 * | 5/2005 | Mendlovic et al. | ........... 359/332 |
| 7,139,295 B2 * | 11/2006 | Tsai et al. | ..................... 372/20 |
| 2003/0010930 A1 | 1/2003 | Thorwirth | |

(Continued)

FOREIGN PATENT DOCUMENTS

DE     19937797 C1     3/2001

(Continued)

OTHER PUBLICATIONS

Buckle et al.; The resonant mirror: a novel optical sensor for direct sensing of biomolecular interactions Part II: Applications; Biosensors & Bioelectronics, 1993, vol. 8; pp. 335-363.

(Continued)

Primary Examiner — Gregory J Toatley
Assistant Examiner — Jarreas C Underwood
(74) Attorney, Agent, or Firm — Hodgson Russ LLP

(57) ABSTRACT

The invention relates to an analytical system and method for generating and metering optical signals. The invention includes an optical system having an illuminating system and a sensor platform. The illuminating system includes an arrangement identified as "SLM" for the temporally rapidly variable spatial light modulation, by which in an operating state, illuminating patterns of a freely selectable and rapidly variable geometry, which can be determined by the settings of the SLM, can be generated on the sensor platform from an illuminating light, which enters into this SLM and which includes a substantially homogenous intensity distribution in the in the cross section of the illuminating light at right angles to its direction of expansion.

28 Claims, 14 Drawing Sheets

U.S. PATENT DOCUMENTS

| | | |
|---|---|---|
| 2003/0138208 A1 | 7/2003 | Pawlak et al. |
| 2004/0038386 A1 | 2/2004 | Zesch et al. |
| 2004/0130787 A1 | 7/2004 | Thome-Forster et al. |
| 2004/0166508 A1 | 8/2004 | Pawlak et al. |
| 2005/0059014 A1 | 3/2005 | Pawlak et al. |
| 2006/0109088 A1 * | 5/2006 | Sagan ............ 340/286.06 |
| 2006/0134669 A1 | 6/2006 | Casasanta, III |
| 2007/0273784 A1 * | 11/2007 | Neil et al. ............ 348/362 |

FOREIGN PATENT DOCUMENTS

| | | |
|---|---|---|
| WO | 0214838 A2 | 2/2002 |
| WO | 02099397 A2 | 12/2002 |

OTHER PUBLICATIONS

Chinowsky et al.; Optimal linear data analysis for surface plasmon resonance biosensors; Sensors and Actuators B, 1999, vol. 54; pp. 89-97.

* cited by examiner

ANALYTICAL SYSTEM COMPRISING AN ARRANGEMENT FOR TEMPORALLY VARIABLE SPATIAL LIGHT MODULATION AND DETECTION METHOD EXECUTABLE THEREWITH

TECHNICAL FIELD

The instant invention relates to an analytical system and to a method executable therewith, for generating and metering optical signals from metering ranges, which are arranged in a one-dimensional or two-dimensional array on a fixed support as metering platform, which will be identified hereinbelow as sensor platform. Such an analytical system and method can be used, for example, for analyzing specimen with reference to biologically, biochemically or synthetically produced substances as analytes contained therein. The invention relates in particular to such a system and method, which is suitable to analyze an individual specimen with reference to a plurality of analytes and/or a plurality of specimens with reference to one or a plurality of analytes on a common sensor platform at the same time. The analytical system according to the invention is thereby suitable for refractive metering methods.

STATE OF THE ART

In the past, numerous embodiments of so-called "microarrays" have become known for simultaneously determining a plurality of analytes, where a plurality of different biological or biochemical or synthetic identification elements are immobilized for specifically identifying and bonding the analytes, which are to be detected, in discrete metering ranges, also referred to as "spots". In many cases, the analyte detection is thereby based on the detection of optical signals, for example of luminescence or luminescence variations of modules, which are capable of luminescence and which are linked with the analyte itself or with one of its bonding partners, which bond with the respective identification elements in one or in a plurality of bonding assay steps in the metering ranges. Such microarrays, where the analytes to be detected from a specimen, which is brought together with the array, bond with the identification elements immobilized in the spots, after they have been identified and "caught" by said detection elements, are also identified as "capture arrays".

In addition to these relatively widely-used "capture arrays", so-called "reverse arrays" or "reverse phase arrays" have also become known in the past, where the specimens themselves, for example cell lysates which are untreated or which are subjected to only a few specimen processing steps, are immobilized in discrete metering ranges in a microarray and the detection elements, possibly linked with luminescent and fluorescent labels, respectively, are supplied to the microarray for the purpose of generating signals in luminescent-based detection methods. Such arrays have been described in International patent applications WO 2004/023142 and WO 2004/023143, for example. The analytical system and method according to the invention can be used in combination with both types of arrays, that is, as "capture arrays" as well as "reverse arrays".

A spatially resolved detection of the light emanating from the metering ranges is advantageous for the detection of the analyte formation, which took place, in different metering ranges, wherein the spatial resolution of the detection step, according to the arrangement of the metering ranges, should be one-dimensional or two-dimensional. For the simultaneous detection of the signals from a plurality of metering ranges, this is typically attained by using corresponding spatially resolved detectors (e.g. line detectors for a one-dimensional spatial resolution or cameras for a two-dimensional spatial resolution).

Based on simple glass or microscope plates and fluorescence detection for the analyte detection, arrays comprising a very high feature density (that is, number of discrete metering ranges per unit of area) are known. Arrays of oligo-nucleotides comprising a density of more than 1000 features per square centimeter are described and claimed, for example, in U.S. Pat. No. 5,445,934. The excitation and the reading of such arrays are based on classical optical arrangements and methods. The entire array can be illuminated simultaneously by means of a widened excitation light beam, which, however, leads to a relatively low sensitivity, because the portion of diffused light is relatively large and because diffused light or underground fluorescent light from the glass substrate is also generated in the area, which does not contain detection elements, which are immobilized for bonding the analyte. To limit the excitation and detection to the areas of the immobilized features and to suppress light generation in the adjacent areas, confocal metering arrangements are used in many cases and the different features are read sequentially by means of "scanning". However, this can lead to a higher expenditure of time for reading a large array and to a relatively complex optical design.

Known are a number of different types of sensor platforms and detection methods, which can be executed therewith, which differ in the used metering principle, for example, and which can accordingly be divided into different categories. For example, a differentiation can be made between luminescence-based detection methods, e.g., based on fluorescence or phosphorescence detection after optical excitation of groups or molecules, which are capable of fluorescence and phosphorescence, which are used in the detection step and refractive metering methods by means of which variations of the index of refraction are detected on the surface of a sensor platform. The refractive metering methods are also identified as "label-free" methods, which are characterized by the advantage that they do not require a "label" and linkage, respectively, of the compound which is to be detected, with a molecular group or compounds, which are to be used specifically for the detection step. In the case of the refractive metering methods, the signals to be detected and the variations thereof can be based on near field effects, for example, which lead to a surface-bound signal amplification (see below).

To improve the sensitivity, evanescence field sensor platforms are used in many cases, that is, such metering platforms, on the surface of which, which faces the specimen to be analyzed, an evanescent field, also identified as being damped at right angles, can be generated. Said evanescent field enables a limitation of an excitation or metering light, which interacts with the analyte and/or the specimen, to the penetration depth of said evanescent field into an adjacent medium to the size of a fraction of the wavelength of the used excitation or metering light. A spatially highly-selective excitation of molecules or interaction with molecules within the penetration depth of this field into the adjacent media is thus possible, while interference signals from the areas beyond said penetration depth can be avoided.

An evanescent field is generated, for example, in response to total reflection of a light beam, which disperses in a medium (e.g. a prism or a self-supporting optical waveguide such as a glass plate) having a higher index of refraction than that of the surrounding medium at the bounding surface of said higher-refracting medium to the low-refracting medium. The evanescent field in such a configuration is thereby generated in each case at discrete locations of the total reflections at the bounding surfaces to the low-refracting medium.

Optical thin-film waveguides, in particular planar optical thin-film waveguides, which, in the simplest case, are a three-layer system, are known as the development of optical waveguides: support material (often also identified as "substrate"), wave-guiding layer, superstrate (and specimen to be analyzed, respectively), wherein the wave-guiding layer has the highest index of refraction. Additional intermediate layers can improve the effect of the planar waveguide even further. The intensity of the evanescent field is thereby highly dependent on the thickness of the wave-guiding layer itself as well as on the ratio of the indexed of refraction of the wave-guiding layer and on the media surrounding said layer. Discrete modes of the guided light can be differentiated with thin waveguides, that is, waveguides having the same layer thickness or a lower thickness than the wavelength to be guided.

Evanescent fields can also be generated by means of so-called "resonant grid structures". Resonant grid structures as well as planar optical waveguides have a structuring (coating) with materials of different indexes of refraction in the direction at right angles to the plane of the substantially planar substrate. At least one of the layers applied to the substrate, into which an excitation or metering light can be coupled under resonance conditions, thereby has a higher index of refraction than that of the substrate. In addition to (in the plane parallel to that of the substrate unstructured) optical waveguides, resonant grid structures have a structuring of the (effective) index of refraction, which extends one-dimensionally or two-dimensionally and which is generated by using the same or different materials, in the plane of the at least one higher-refracting layer parallel to the substrate plane. Furthermore, a resonant grid structure can also have a structuring with materials of different indexes of refraction, such as in the direction at right angles to the substrate plane, in the plane, which is parallel thereto. Resonant grid structures are known from the literature and are described in U.S. Pat. No. 5,598, 300 as well as in patent application US 2004/0130787, for example.

So-called "resonant mirrors" can be considered to be a further embodiment of evanescent field sensor platforms. They substantially comprise a three-layer system: a high-refracting prism, a layer with a lower index of refraction applied thereon below a further layer having a high index of refraction located thereon. Under operating conditions, light irradiated onto the prism is completely reflected on the surface of said prism. The evanescent field created on the surface of the prism in response to said complete reflection extends into the layer having a low index of refraction and due to the small thickness of the low-refracting layer, it also extends into the high-refracting second layer. The second high-refracting layer thereby acts like a waveguide. The effective index of refraction of this waveguide and thus the expansion speed of the light in this waveguide is thereby determined by means of the optical parameters of the layer system (substantially indexes of refraction and layer thicknesses) as well as by means of a coating (e.g. with an adhesion promoting layer or with specific detection elements for the analyte detection), which are possibly located on the surface of the evanescent field sensor platform as well as by means of the surrounding medium. When the expansion speed of the evanescent field of the prism corresponds to the expansion speed of the light in the waveguide, a portion of the evanescent field of the prism is coupled into the waveguide. The expansion speed of the evanescent field of the prism can be influenced, for example by varying the angle of incidence or by varying the wavelength. Evanescent fields are in turn created on both sides of the waveguide by means of the light guided in the waveguide, whereby the evanescent field of the waveguide on the prism side in turn extends into the low-refracting layer and beyond it into the high-refracting prism. Analogously to the coupling into the waveguide, light guided in the waveguide is thus again uncoupled into the prism and can be directed onto a detection unit from that location. The processes of light coupling and uncoupling, which are bound to the prism as well as to the second high-refracting layer, take place at the same time, whereby the light directed from the prism to the detection unit has a resonant characteristic. This technology of the "resonant mirror" is described in more detail, for example, in U.S. Pat. No. 5,255,075 as well as in the publication P. E. Buckle et al., "The resonant mirror: a novel optical sensor for direct sensing of biomolecular interactions, Part II: Application", Biosensors & Bioelectronics 8 (1993), 355-363.

The use of evanescent field sensor platforms is suitable to solve the problem of attaining an improved sensitivity, that is, lower detection limits in response to the analyte detection, and higher accuracy.

In addition, however, there is a necessity to optimize analytical systems and detection methods for the metering of the highest possible number of signals from a plurality of discrete metering ranges within the shortest possible period of time.

Known are, for example, imaging techniques and analytical systems equipped for this. Metering arrangements comprising a simultaneously more or less large-surface illumination of a plurality of metering ranges on a sensor platform, for example for absorbing luminescence and fluorescence signals from microarrays on a thin-film waveguide as sensor platform, are known from the state of the art from International application WO 02/21110 or of signals of a large-surface grid coupling sensor (also based on a thin-film waveguide; more detailed explanation will follow) from International application WO 01/88511. These arrangements make it possible to absorb signals from a plurality of metering ranges within relatively short metering times, which are determined by the illuminating period.

It is a disadvantage of these arrangements, however, that, due to the continuous large-area illumination of the sensor platform, which is not limited to the areas of the metering ranges, in particular signals from the intermediate areas between the metering ranges can lead to an increased basic signal, which is not caused by the presence of an analyte, which, due to the resulting increase of the level of the basic signal, leads to a reduced signal-to-noise ratio and which can thus lead to a reduced sensitivity for the determination of a plurality of analytes as compared to the sensitivity for a single analyte determination in a single metering range with an excitation, which is limited thereto and to a detection on a sensor platform of an otherwise similar technical design. Furthermore, there is a higher risk of an optical crosstalk of the signals from the different metering ranges in response to a continuous large-area illumination.

The risk of the crosstalk of optical signals from different metering ranges is bypassed by means of scanning arrangements, that is, by means of sequential illumination and signal detection of different discrete metering arrangements. In particular in the case of sensor platforms having large dimensions, for example in the format of a standard microtiter plate, extended total times for the signal absorption and possibly also extensive mechanical positioning devices for necessary translations across large traverse paths, combined with very high demands on the positioning accuracy, are to be expected, which can additionally lead to a disadvantageous increase of the system costs.

The object is thus to provide for an analytical system and a method, which can be executed therewith, whereby it is made possible to analyze a specimen within a short period of time with reference to a plurality of analytes contained therein and/or to analyze a plurality of specimens with reference to one or a plurality of analytes contained therein at a high sensitivity, as it is known, for example, from evanescent sensor platforms for individual analyte determination and which is to be further improved by increasing the signal-to-noise ratio, if possible combined with a simultaneously reduced risk of an optical crosstalk between signals from different metering ranges.

BRIEF DESCRIPTION OF THE INVENTION

According to the invention, the afore-mentioned object is solved by means of an analytical system for generating and metering optical signals and/or the variations thereof from metering ranges, which are arranged in a one-dimensional or two-dimensional array on a substantially optically transparent sensor platform, at least comprising
  an optical system comprising an illuminating system for illuminating metering ranges on the sensor platform and a detection system comprising at least one detection unit for detecting signals from the metering ranges on the sensor platform, in the direction of the transmission or reflection of the illuminating light in a spectral range, which comprises the spectral range of the illuminating light, and
  a sensor platform, which can be inserted into the optical system, comprising metering ranges, which are arranged thereon in a one-dimensional or a two-dimensional array,
characterized in that the illuminating system comprises an arrangement identified as "SLM" for the temporally rapidly variable spatial light modulation by means of which in the operating state illuminating patterns of a freely selectable and rapidly variable geometry, which can be determined by the settings of the SLM, can be generated on the sensor platform from an illuminating light, which enters into this SLM and which comprises a substantially homogenous intensity distribution in the cross section of the illuminating light at right angles to its direction of expansion.

"Rapidly variable" spatial light modulation and "rapid variation" of the illuminating pattern is thereby understood to mean that these variations take place at a frequency of greater than 1 Hz, preferably greater than 1 kHz, in particular greater than 1 MHz.

The freely adjustable geometry of the illuminating pattern on the sensor platform makes it possible to specifically illuminate metering ranges in any arrangement and geometry on the sensor platform and to specifically shadow areas between the metering ranges so that the generation of impairing scatter signals or interference signals from these neighboring areas can be avoided. The illuminating pattern can thereby be varied at a high speed. An extremely rapid optical "scanning" of the entire surface of the sensor platform with limitation of the signal excitation to the metering ranges themselves and the detection of the signals from a plurality of metering ranges is thus made possible in an advantageous manner, wherein the afore-mentioned disadvantages of scan arrangements and methods are avoided at the same time.

As compared to the state of the art, the analytical system according to the invention has further considerable advantages:
  The mechanical tolerances of the accommodating system of the analytical system for a sensor platform, which is to be inserted, can be determined in a relatively broad manner, because fluctuations in the dimensions and in the positioning, respectively, of a sensor platform, which is to be inserted, can be compensated by adaptations of the illuminating pattern. The demands on the tolerances of the dimensions of the sensor platforms can thereby furthermore be kept in a broad manner, which lowers the production costs thereof.
Preferred embodiments of the analytical system according to the invention comprising a plurality of individually controllable individual elements of the SLM, which is preferably greater than the number of the metering ranges, allow for a high spatial resolution of the signal generation and thus also of the signal detection and different forms of sub-sampling.
In the case of the illumination of metering ranges by means of a plurality of individual elements of the SLM, a plurality of metering values can be generated simultaneously per metering range independent on one another.
An adaptation or even a variation or exchange of the optical elements of the to analytical systems is not required in response to a variation of the geometric arrangement of metering ranges on the sensor platform, but the illuminating pattern can be adapted accordingly.
The use of diffractive optical elements, which often generate a rigid, invariable illuminating pattern, can be dispensed with in the light paths. In particular, the otherwise necessary change and exchange thereof, respectively, can be avoided in response to variations to the light source or the mentioned geometric characteristics of the sensor platform.
Broad-band light sources can also be used, which is rarely possible in combination with diffractive optical elements in the illumination light path.
The rapid changeability of the generated illuminating pattern allows for the adaptation thereof to dynamic processes (e.g. the growth or the contraction of biological cells).
Different metering ranges can have a random, different form, which is independent on one another.
"Binning" or similar functions can be used.
A use of additional masks in the light paths is not required.
The total number of optical components of the system can be reduced, which leads to a reduction of the system costs: a plurality of diffractive optical elements and masks can be replaced by a single SLM.

A further object of the instant invention is a method for generating and metering optical signals and/or the variations thereof from metering ranges, which are arranged in a one-dimensional or two-dimensional array on a substantially optically transparent sensor platform, using an analytical system according to one of the below-described embodiments, at least comprising
  an optical system comprising an illuminating system for illuminating metering ranges on the sensor platform comprising an arrangement identified as "SLM" for a temporally rapidly variable spatial light modulation as well as comprising a detection system comprising at least one detection unit for detecting signals from the metering ranges on the sensor platform in the direction of the transmission or reflection of the illuminating light in a spectral range, which comprises the spectral range of the illuminating light, and
  a sensor platform, which can be inserted into the optical system, comprising metering ranges which are arranged thereon in a one-dimensional or two-dimensional array, characterized in that in the operating state, illuminating patterns of a freely selectable and rapidly variable geometry, which can be determined by the settings of the SLM, can be generated on the sensor platform from an illuminating light, which enters into this SLM and which comprises a substantially homogenous intensity distribution in the cross section of the illuminating light at right angles to its direction of expansion.

An embodiment of the method according to the invention, which is characterized in that the optical signals and/or the variations thereof are generated from metering ranges by one or a plurality of bonding or adsorption results between one or a plurality of analytes in one or a plurality of specimens and specific detection elements for said analytes in or on said metering ranges is particularly preferred thereby, wherein the specimens and the detection elements for the analytes, which are to be detected in the specimens, are brought into contact with one another on the metering ranges and that a simultaneous qualitative and/or quantitative detection of a plurality of analytes is made possible in one or a plurality of specimens and/or of one or a plurality of analytes in a plurality of specimens from these optical signals and/or from the variations thereof.

DETAILED DESCRIPTION OF THE INVENTION

Figure 1:
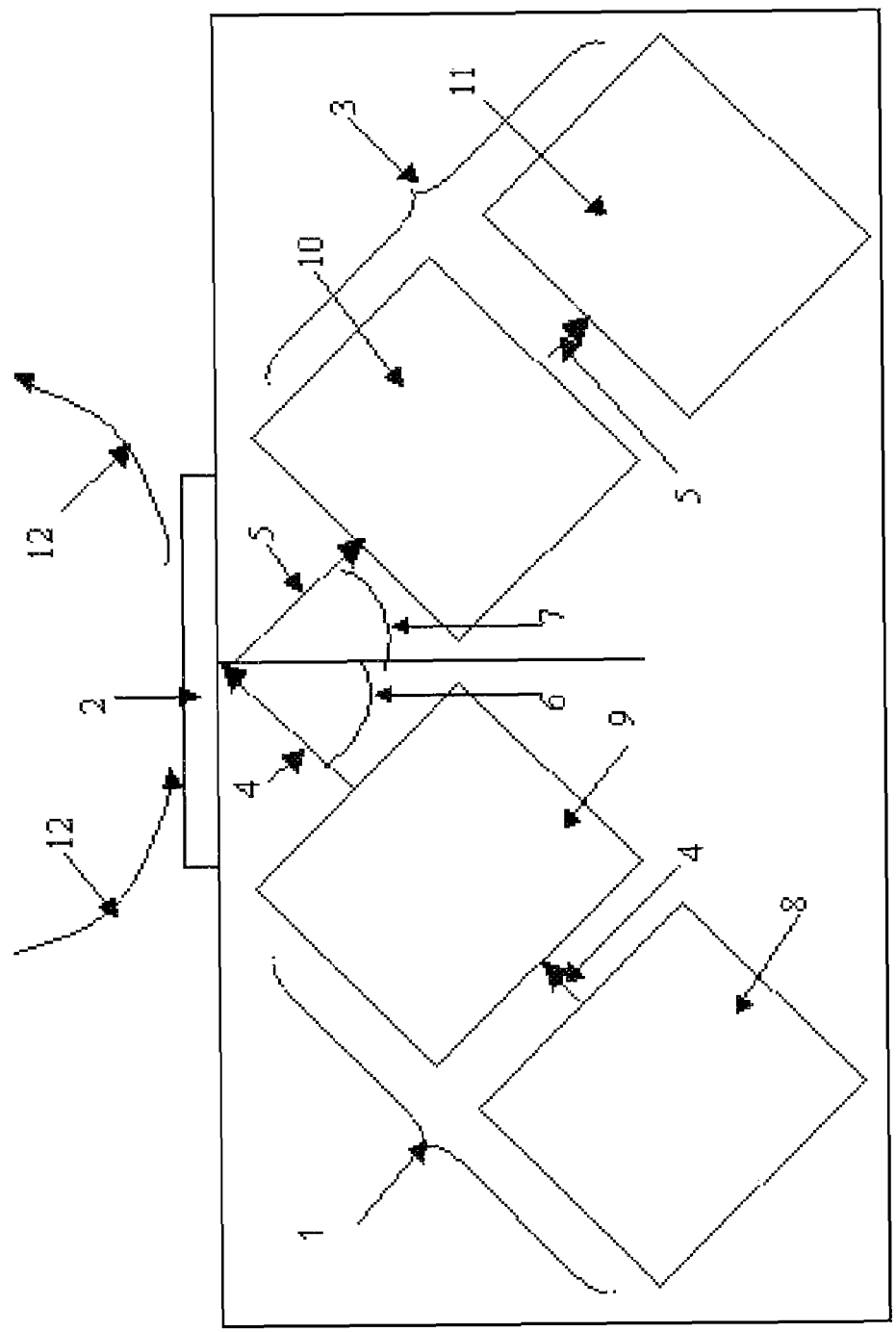
FIG. 1 shows schematically a first embodiment of an analytical system according to the invention, where the illuminating system 1 and the detection system 3 are arranged on the same side with reference to the sensor platform 2.

In terms of the instant invention, metering ranges are to be defined in each case by means of the closed surface, which is displayed on a sensor platform for detecting a single metered variable, that is, they are to be used for generating an individual signal value. The sensor platform can be embodied as a microtiter plate, for example, comprising a plurality of wells, which are arranged in a matrix-like manner, and a thin-film waveguide comprising grids structured therein as ground. For example, the ground area of an individual well can then represent a metering range, on which the index of refraction of a liquid filled into the well is determined by means of a refractive metering. However, the ground area of an individual well can also serve the purpose for detecting a plurality of metered values for simultaneously detecting a plurality of analytes in a specimen, which is filled into an individual well. In accordance with the aforementioned broad definition, metering ranges are then to be defined by the closed surfaces, which capture compounds to be detected, which are immobilized at that location or specific bonding partners, which are immobilized at that location, for detecting one or a plurality of analytes in one or a plurality of specimens in a bioaffinity assay. These surfaces can thereby have any geometry, for example the shape of circles, rectangles, triangles, ellipses, etc. Preferably, the metering ranges are a plurality of metering ranges. Discrete metering ranges, which are separated laterally or spatially, are used in a particularly preferred manner.

In a one-dimensional or two-dimensional arrangement, the sensor platform preferably comprises more than 50, particularly preferably more than 500, even more preferably more than 50000 metering ranges.

There is a multitude of known types or methods for mustering and immobilizing, respectively, the compounds, which are to be detected or specific bonding partners on a sensor platform. This can take place by means of physical adsorption or by means of electrostatic interaction, for example. The orientation of the immobilized compounds or of the specific bonding partners is then generally statistical so that only a portion thereof can be accessed for a bond with a bonding partner, which is to be supplied in a specimen. Furthermore, there is a danger that a portion of the immobilized compounds or bonding partners is rinsed off in response to a different composition of the specimen, which contains the analyte or in response to reagents, which are used in the detection process. It can therefore be advantageous when an adhesion-promoting layer is applied to the surface of the sensor platform, which is to be used for the signal generation, for the purpose of a more stable immobilization. This adhesion-promoting layer should be optically transparent. In particular in the case of an evanescent field sensor platform (see below) it is preferred for the adhesion-promoting layer not to project from the high-refracting layer of the sensor platform into the adjoining medium beyond the penetration depth of the evanescent field. The adhesion-promoting layer should thus have a thickness of less than 200 nm, preferably less than 20 nm. It can comprise, for example, chemical compounds from the group silanes, epoxides, functionalized, charged or polar polymers and "self-organized functionalized monolayers".

Compounds or specific bonding partners, which are to be immobilized on a sensor platform, in particular also specific identification elements, which are to be immobilized, as well as the analytes, which are to be detected, are preferably chosen from the group, which is formed from nucleic acids (for example DNA, RNA, oligo-nucleotides), nucleic acid analogs (e.g., PNA), antibodies, aptamers, membrane-bonded and isolated receptors, the ligands thereof, antigens for antibodies, "histidine-tag-components" etc. Complete biological cells or components thereof can also be immobilized on a sensor platform.

An individual metering range on a sensor platform can include a single type of compounds, for example for detecting an individual analyte in a specimen, which is to be supplied. This is preferred in the case of "capture arrays", which are to be generated. However, an individual metering range can also include a plurality of different compounds. This is the case in the case of "reverse arrays", where an individual metering range is formed in each case by means of the closed surface on the sensor platform, which is assumed by a specimen, which is immobilized there and which comprises a plurality of different compounds, which are included therein and which are to be detected as analytes.

Different embodiments of sensor platforms are suitable as sensor platforms, which can be inserted into the optical system of the analytical system according to the invention. The sensor platform is to be substantially optically transparent at least at the wavelength of the illuminating system. "Substantially optically transparent" as a characteristic of the sensor platform, which can consist of different layers for example, is thereby understood to mean that light of the wavelength of the illuminating light in response to expansion in the volume of the material or a layer material of the sensor platform across a distance of 5 mm experiences a weakening by means of absorption of no more than 80%, preferably of no more than 50%, particularly preferably of no more than 20%. Expansion losses caused by boundary layer diffusion, for example in response to light conductance in a film waveguide due to surface roughness or surface structuring such as, for example, a surface relief grid acting in a diffractive manner, are not to be considered with this definition of "substantially optical transparency", even if they are to actually prevent the further light expansion. The afore-mentioned demand on the "substantially optical transparency" of the sensor platform, however, excludes coatings, for example, comprising absorbing metals such as gold and silver, as they are used, for example, for sensor platforms for generating surface plasmon resonances and where the expansion of a "coupled light" takes place only via a length in the range of several hundred micrometers and thus also excludes such sensor platforms per se. In a single-layer or multi-layer system, the material of the sensor platform preferably comprises a material from the group, which is formed from substantially optically transparent glasses, plastics and ceramics, wherein layers of these materials can optionally be provided with additional coatings.

It is preferred that the side of the sensor platform on which the discrete metering ranges are generated, is substantially planar. "Substantially planar" is thereby understood to be that the radius of curvature of the surface of this side is greater than 10 cm in the area of the metering ranges. According to this definition, an embodiment of a sensor platform, which is embodied as a microtiter plate, comprising the ground areas of the wells as metering range is also considered to be "substantially planar", because the above definition is fulfilled in each case for the area of these metering ranges. It is furthermore preferred that the waviness of the surface of the sensor platform comprising the metering ranges is less than 0.2 nm in the area of the metering ranges. It is furthermore preferred that the roughness of the surface of the sensor platform comprising the metering ranges is less than 20 nm in the area of the metering ranges, particularly preferably less than 2 nm, even more preferably less than 1 nm. The preference with reference to the surface roughens applies in particular for the embodiments embodied as evanescent field sensor platforms (see below) so as to minimize expansion losses of light by diffusion at the surface, which is provided with the metering ranges. Additional surface structuring, such as diffractively acting surface relief grids or other additionally applied surface structures are not to be considered for this preference with reference to the "surface roughness" and for the definition thereof.

A preferred embodiment of the analytical system according to the invention is characterized in that the sensor platform is embodied as an evanescent field sensor platform.

It is preferred thereby that the sensor platform is chosen from the group of prisms for generating internal total reflection, self-supporting optical waveguides, optical thin-film waveguides, thin-film waveguides comprising grids structured therein for the light coupling and/or uncoupling, resonant grid structures as well as "resonant mirrors".

It is preferred thereby for embodiments of an analytical system according to the invention comprising a thin-film waveguide or a thin-film waveguide comprising grids structured therein as evanescent field sensor platform that the support material of the waveguiding layer and the layer adjoining the waveguiding layer in the direction of the side of the waveguiding layer facing away from the metering ranges, respectively, has the lowest possible index of refraction, because the expansion of the evanescent field is hereby advantageously impacted in the direction of the metering ranges on the opposite side of the waveguiding layer: in the case of an asymmetrical distribution of the indexes of refraction of the layer, which are adjacent to the waveguiding layer, the maximum of the intensity guided in an optical waveguide, relating to the cross section of the film waveguide, is arranged so as to be asymmetrical in the direction of the adjacent layer comprising the higher index of refraction. Preferably, the index of refraction of the support material and of the layer adjoining the waveguiding layer in the direction of the side of the waveguiding layer facing away from the metering ranges, respectively, is less than 1.6, particularly preferably less than 1.5, even more preferably less than 1.4. Thermoplastic materials, for example, such as polyvenylidenfluoride, polymethylpentene, cycloolefin copolymers (COC) or cycloolefin polymers (COP) and mixtures of polyvenylidenfluorides and polymethylmethacrylates are suitable for this as materials comprising correspondingly low indexes of refraction. Even fluoropolymers such as fluoroacrylate comprising an index of refraction of less than 1.4 are known. In response to the use of the sensor platform for the analysis of liquid or aqueous specimens, support materials comprising the smallest possible liquid and water absorption are advantageous. At the same time, it is advantageous when the waveguiding layer has the greatest possible index of refraction, preferably greater than 1.8, particularly preferably greater than 2.0. Metal oxides such as $TiO_2$, $Ta_2O_5$, $Nb_2O_5$, ZnO, $HfO_2$, $ZrO_2$, $TiO_2$—$SiO_2$, $Al_2O_3$, $Si_3N_4$, HfON, SiON are particularly well suitable as materials of the waveguiding layer. Such embodiments of sensor platforms, which are suitable for an analytical system according to the invention, are also described in U.S. application number 2005/0025421 with FIG. 13 (production of a "microplate" according to a microtiter plate with thin-film waveguides comprising grids structured therein in the ground of the wells of the microtiting plate), FIGS. 7, 8 and 9 (index of refraction and distribution of the mode intensity, that is, the intensity of the guided light), which are hereby completely introduced into this application together with the corresponding portions of the description.

In refractive metering methods using an evanescent field sensor platform, the variation of the so-called effective index of refraction is used for an analyte detection due to variations of the area density by molecular adsorption or desorption on the sensor platform or variations of the macroscopic index of refraction of a surrounding medium in the evanescent field of the sensor platform. The effective index of refraction is a function of the macroscopic index of refraction of the high-refracting, waveguiding layer and the thickness thereof, the indexes of refraction and layer thicknesses of adjacent layers or media as well as of the mode arrangement of the light, which is to be coupled into the waveguiding layer via the grid, of the polarization (e.g., transverse electric (TE) or transverse magnetic (TM) polarization) as well as of the wavelength of an irradiated illuminating light.

At a constant wavelength of the irradiated illuminating light, the variations of the effective index of refraction leads to variations of the angle of resonance with reference to the surface normal of the sensor platform for the light coupling or uncoupling from a grid coupling sensor platform. These variations of the angles of resonance can be determined from the signals and the variations thereof, which are supplied by the detection system (comprising one or a plurality of detectors) of the analytical system according to the invention. In the case of an angle of irradiation or the illuminating light, which is maintained so as to be constant, variations of the resonance wavelength for the light coupling or uncoupling are determined from a grid coupling sensor platform from the corresponding detector signals, at a variable polychromatic spectrum of the illuminating light or via a certain spectral range (e.g. in the range of 1-20 nm). The state of the art relating to the use of grid coupler sensor platforms is described, for example, in U.S. Pat. Nos. 4,815,169, 6,455,004 and 6,429,022 as well as in publications K. Tiefenthaler, W. Lukosz, "Sensitivity of grating couplers as integrated-optical chemical sensors", J. Opt. Soc. Am. B6 (1989) 209 ff., W. Lukosz, P. M. Nellen, C. Stamm, P. Weiss, "Output grating couplers on planar waveguides as integrated, optical chemical sensors", Sensors and Actuators B1 (1990) 585 ff. and T. Tamir, S. T. Peng, "Analysis and design of grating couplers", Appl. Phys. 14 (1977) 235-254.

The use of injection molding, hot stamping, holographic light exposure or so-called nano-imprint-lithography as well as the techniques described in U.S. Patent Application 2003/0017581 and in U.S. Pat. No. 6,873,764, for example, is known to the person of skill in the art for producing coupling grids. Typically, the grid structures are initially generated as surface structures in a surface of the substrate, whereupon at least one dielectric layer comprising a preferably higher index of refraction than that of the substrate and comprising a controlled layer thickness (of 50 nm to 500 nm, for example) is applied directly or onto optional intermediate layers in a subsequent step and the structure generated on the substrate typically transfers into the surface of this dielectric layer during the application step. "Resonant Mirror" sensor platforms are generated by applying dielectric layers comprising a varying index of refraction and an accurately defined layer thickness on substrates, which are substantially optically transparent at least in response to the wavelength of the illuminating light.

In particular for the purpose of a compatibility with inserted laboratory robots and the standard equipment of chemical and analytical laboratories, it is advantageous when the sensor platform has the basic dimensions of a microtiter plate according to SBS standard (approx. 85.5 mm×127.8 mm) or when it is embodied as component of a microtiter plate. This includes that the sensor platform itself can represent a microtiter plate. Such arrangements are also described in US 2005/0110989 (FIG. 2-FIG. 6 and FIG. 14-FIG. 16), U.S. Pat. No. 5,738,825 (FIG. 1-FIG. 3, FIG. 5-FIG. 7) and U.S. Pat. No. 6,018,388 (FIGS. 1-4), the mentioned figures of which and corresponding descriptions of which are hereby completely introduced as part of the instant application. When the sensor platform is embodied as a microtiter plate, it can comprise, for example, 96, 384 or 1536 specimen containers or "wells" according to the industrial standard productions.

With reference to the arrangement relating to the temporally variable spatial light modulation, it is preferred that it is chosen from the group of "Digital Mirror Devices" DMD, liquid crystal displays LCD, "Liquid Crystal on Silicon Silicon" LCOS microdisplays and mechanically movable masks comprising light-permeable and light-blocking areas.

It is preferred that the arrangement for the temporally variable spatial light modulation comprises a plurality of individual elements in a one-dimensional or two-dimensional arrangement, which can be switched discretely for the transfer to the sensor platform or for blocking the illuminating light. It is preferred thereby that at least one of these individual elements corresponds to a metering range. It is particularly preferred that a metering range of a plurality of these individual elements is illuminated. When using a plurality of individual elements per metering range, the illuminating pattern can approach the exact form of the metering ranges, such as rectangles, triangles, circles, hexagonal forms or arbitrary forms, for example, such as they can appear in response to the metering of cells, for example, to a better and simpler extent and an illumination of areas, which do not belong to the metering ranges can be avoided for the most part, which leads to an improved signal-to-noise ratio.

However, one or a plurality of individual elements can also be used in each case for illuminating areas between the metering ranges, for example for generating background signals, calibrating signals or referencing signals, which can be used for evaluating the signals from the metering ranges.

It is particularly preferred thereby that the arrangement for the temporally variable spatial light modulation comprises a plurality of individual elements in a two-dimensional arrangement, which can be switched discretely for the transfer to the sensor platform or for blocking the illuminating light. Preferably, these are more than 100×100 individual elements in a two-dimensional arrangement, which can be switched discretely.

The illuminating pattern generated by the arrangement for the temporally variable spatial light modulation comprises a plurality of illuminated or shadowed areas in the cross section of the light path of the illuminating light and on the sensor platform, which will subsequently also be identified as "pixel of the illuminating light".

It is furthermore advantageous when an individual element of the arrangement for the temporally variable spatial light modulation has a response time of less than 20 msec for the change between positions or settings for transferring to sensor platforms or for blocking the illuminating light.

It is advantageous in particular for metering on cells, which are immobilized on the sensor platform, when the arrangement for the temporally rapidly variable spatial light modulation enables the generation of rapidly variable illuminating patterns on the sensor platform, whereby objects comprising a geometry, which varies temporally, can be specifically illuminated on the sensor platform as metering ranges comprising a geometry which varies temporally and light emanating from these objects can be detected.

The illuminating system of the analytical system according to the invention can comprise one or a plurality of polychromatic or substantially monochromatic light sources. A "substantially monochromatic" light source is thereby to be understood to be such a light source, the spectral emission width of which is less than 5 nm.

The one or plurality of polychromatic or substantially monochromatic light sources can be chosen from the group of lasers "Vertical Well Surface emitting Lasers" VCSEL, edge-emitting laser diodes, superluminescent diodes SLD, light-emitting diodes LED, organic light-emitting diodes (OLED), gas discharge lamps and light bulbs.

It is preferred that before the illuminating light enters into the arrangement for the temporally variable spatial light modulation, the illuminating system in the optical light path comprises optical or electro-optical components for producing an intensity distribution of the illuminating light, which is homogenous across the illuminating cross section, wherein these components are preferably chosen from the group of optical projection systems, micro tens arrays, "light tunnels" and light rods" or large-surface emitting light sources comprising a plurality of individual light sources, such as LEDs or OLEDs having a different or the same emission wavelength, the total emission of which is formed into a homogenous light distribution by means of diffractively or refractively acting components. Arrangements of large-surface homogenous illuminating systems comprising liquid crystal displays can also be used. The light of a rod-shaped light source is thereby coupled into a planar light guide, in which the light is guided within the light guide by means of total internal reflection. Diffractive structures, which specifically guide a portion of the light out of the light guide, are applied to a surface of the light guide. In response to a suitable selection of the diffractive structures, the surface of the light guide acts as a virtually homogenous light source. Due to a liquid crystal display applied to the surface, the light intensity of the homogenous illumination can be spatially illuminates. Such an arrangement is described in U.S. Pat. No. 6,976,779, for example.

"Light rods" or "light tunnels", such as LightTunnel™ (Unaxis, Balzers, Liechtenstein), for example, are used in standard projection systems and are based on the following functional principle: the light of one or a plurality of light sources is focused into a front side of the optical component, which is identified as "light tunnel" or as "light rod" and which is embodied as a hollow body, preferably having a cuboid or cylindrical shape, the optical inner sides of which are metalized. Such preferably cuboid or cylindrical bodies comprising a transparent material—mostly glass or plastic— and in which the guiding of light is carried out by means of internal total reflection (TIR), are thereby identified as "light rods". After multiple reflections on the insides of such a "light tunnel" or "light guide", the light escaping on the opposite front side has an increased homogeneity of the intensity distribution across the illuminating cross section.

It can furthermore be advantageous when optical components acting in a telecentric manner are arranged in the optical light path of the illuminating light, before the illuminating light enters into the arrangement for the temporally variable spatial light modulation or in the further light path in the direction of the sensor platform. Telecentric lenses, as they are described for example in U.S. Pat. No. 6,324,016 (see FIGS. 1-6), enable the elimination of perspective disturbances and an improved illustration of objects, which are arranged outside of the optical axis of an optical system. The disclosure of FIGS. 1-6 of U.S. Pat. No. 6,324,016 is hereby completely introduced into the instant application together with the corresponding portions of the description.

For the case of an angle of irradiation, which is not perpendicular but different from zero (measured from the surface normal of the substantially planar sensor platform) of the illuminating light onto the sensor platform, that is, in the case of an oblique light incidence, it may be advantageous when the optical system comprises provisions for corrections relating to the compensation of oblique light incidence according to Scheimpflug, as they are described, for example, in standard photography textbooks.

The detection system of the analytical system according to the invention can comprise one or a plurality of detection units from the group of photodiodes, photomultipliers, avalanche diodes, CMOS arrays and CCD cameras.

It is preferred that the detection system comprises one or a plurality of spectrally splitting electro-optical components for a spectrally selective detection of the light emanating from the metering ranges. These may be, for example, spectrometers, spectrally selective optical filters such as short or long pass filters, optical broadband filters or so-called notch filters, which are adapted to laser emission lines.

It is preferred that the illuminating system and/or the detection system comprise polarization-selective components in the light path. It is thereby particularly advantageous when the components acting in a polarization-selective manner enable the differentiation between light, which is polarized in a transverse electric (TE) and transverse magnetic (TM) manner, which emanates from the metering ranges on the sensor platform.

Embodiments of an analytical system according to the invention, which are characterized in that the index of refraction and/or the thickness of an adsorbed layer or the variation thereof in or on the metering ranges on the sensor platform can be determined from the signals of the one or plurality of detectors and from the variations thereof are furthermore preferred. This may be, for example, the macroscopic index of refraction of a liquid, which is brought into contact with one or a plurality of metering ranges, or the variations thereof.

It is preferred that the light detected by means of the detection system is analyzed, wherein the intensity or the intensity pattern is preferably evaluated. In the case of a resonance curve, for example, the metered signal can be evaluated by means of the most different methods, which are known to the person of skill in the art, such as described in U.S. Pat. No. 4,815,843 (column 6, last paragraph, etc.), for example. Methods, however, whose evaluation method and results determined therewith are virtually or even completely unaffected by the absolutely measured intensities on the detector, are particularly preferred. U.S. Pat. No. 6,429,022 (FIG. 12) provides an example of how an arbitrarily measured intensity pattern can be used. A preferred embodiment of a method for generating and metering optical signals and/or the variation thereof can be inferred herefrom. Said embodiment is characterized in that a brightness distribution of the signals is metered by means of the detection system comprising at least one detection unit and that this brightness distribution is analyzed independent on metered absolute signal intensities (also see one of the sections following below in this description).

Generally, it is advantageous for the evaluation of the light intensity measured by means of the detection system to use methods, where the searched metering value, for example the position of a resonance curve, can be determined by means of methods, where the method, which is preferred for the examination, can barely or not at all be determined by the absolutely measured intensity, but by means of a virtually or completely intensity-independent method, such as, for example, in the subsequently described methods for determining the position of the resonance curve.

In the example of a resonance curve, a preferred method for determining the variation of the position of the resonance is based on the fact that the intensity is measured on the shoulders of the resonance curve. When using the first derivative of the resonance curve, the variation of the position of the resonance curve can be computed from the variation of the intensity of the detected light. The variation of the effective index of refraction can then for example be determined and computed from the variation of the position of the resonance curve, as it is described, for example, in the state of the art relating to the use of grid coupling sensor platform.

A further preferred method for determining the variation of the position of a resonance curve is based on the determination of the center of gravity of the metered resonance curve, which clearly allows for conclusions relating to the position of the resonance curve. The center of gravity varies accordingly in response to a small variation of the resonance position.

A further preferred method for determining the position of a resonance curve is based on the use of a model curve, for example a Lorentz or Gauss curve. The model curve is adapted to the metered curve by means of numerical methods, which is also known as "numerical fitting". Commercial software for the fitting of model curves is offered by OriginLab (Northampton, Mass. 01060, USA), for example. The searched position of the metered resonance curve can be determined from the position of the model curve.

Embodiments of an analytical system according to the invention, for example evanescent field sensor platforms, which make it possible for the effective index of refraction and/or the variations thereof in or on the metering ranges on the sensor platform to be capable of being determined from the signals of the one or plurality of detectors and/or from the variations thereof, are particularly preferred.

A possible embodiment is thereby characterized in that the angle of resonance for coupling illuminating light into a thin-film waveguide via a grid structured therein and/or variations of such an angle of resonance with reference to the surface normal of the sensor platform can be determined from the signals of the one or plurality of detectors and from the variations thereof in response to a wavelength of the illuminating light, which is irradiated constantly.

Another possible embodiment is characterized in that the resonance wavelength for coupling illuminating light into a thin-film waveguide via a grid structured therein and/or variations of such a resonance wavelength can be determined from the signals of the one or plurality of detectors and from the variations thereof in response to a constant angle of irradiation of the illuminating light with reference to the surface normal of the sensor platform.

The irradiation of the illuminating light and the detection of the light emanating from the metering ranges can be carried out from opposite sides with reference to the surface of the sensor platform comprising the metering ranges located thereon. Preferably, however, the irradiation of the illuminating light and the detection of the light emanating from the metering ranges take place on the same side of said surface.

The angle of irradiation of the illuminating light on the sensor platform can be in the range from −90° to +90° (+90° and −90° are thereby equivalent with "parallel to the surface of the sensor platform"), wherein the angle range between −60° and +60° is preferred. The illuminating light can be polarized, for example polarized in a transversal electric (TE) or transversal magnetic (TM) manner. In the case of illuminating light, which is polarized in a TM manner, an angle of irradiation is particularly preferred close to the Brewster angle for the inflow of light of the illuminating light into the sensor platform on the surface side thereof, which faces away from the metering ranges, because Fresnel reflections do not appear from this bounding surface of the sensor platform in response to this angle of irradiation.

In the case of the irradiation of the illuminating light and detection of the light emanating from the metering ranges on the same side with reference to the surface of the sensor platform comprising the metering ranges located thereon, the detection takes place so as to be rectified to the reflection direction of the illuminating light, thus also in an angle range between −90° and +90°, wherein an angle range between −60° and +60° is preferred and the detection under the Brewster angle is in turn preferred for the case of TM-polarized illuminating light.

Such a configuration of an analytical system according to the invention is illustrated in FIG. 1. The illuminating system 1 of the analytical system according to the invention consists of an illuminating unit 8, which comprises a light source and an arrangement identified as "SLM" for the temporally rapidly variable spatial light modulation, and an illuminating optics 9. According to this illustration, the illuminating light 4 is irradiated under an angle of irradiation 6 of approximately 45° to the surface normal of the rear side, that is, the side of the sensor platform 2 facing away from the metering ranges. The metering ranges (not illustrated) are located on the upper opposite side surface of the sensor platform 2 in the image plane. Specimen, test, calibration or reference provision in liquid or gaseous from, which is supplied in the metering ranges and which is dissipated again after interaction with the metering ranges, is indicated by means of the curved arrows 12 and 12'. The detection angle 7 for detecting the light emanating from the sensor platform 2 and from the metering ranges arranged thereon, respectively, is chosen to be the same as the reflection angle, thus approximately 45° in this case. The detection system 3 comprises a light collecting optics 10, for example one or a plurality of collective lenses and a detection unit 11.

Figure 4:
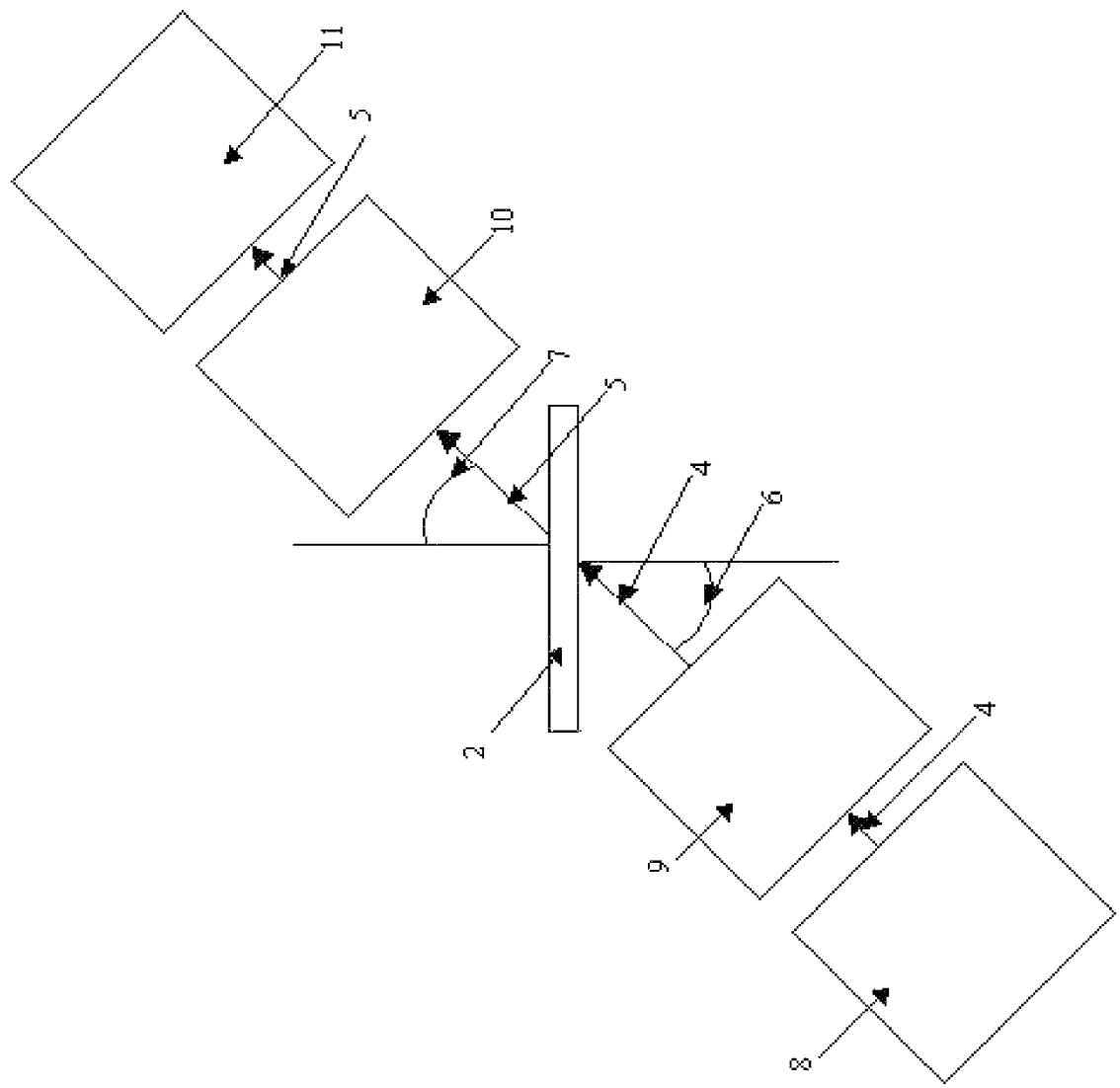
FIG. 4 shows schematically an embodiment of an analytical system according to the invention, where the illuminating system and the detecting system are arranged on opposite sides with reference to the sensor platform and where the detection takes place in the direction of the transmitted light.

A configuration, which is analogous to the configuration in FIG. 1, with the detection system not being arranged in the reflection but in the transmission direction, is illustrated in FIG. 4.

Figure 2:
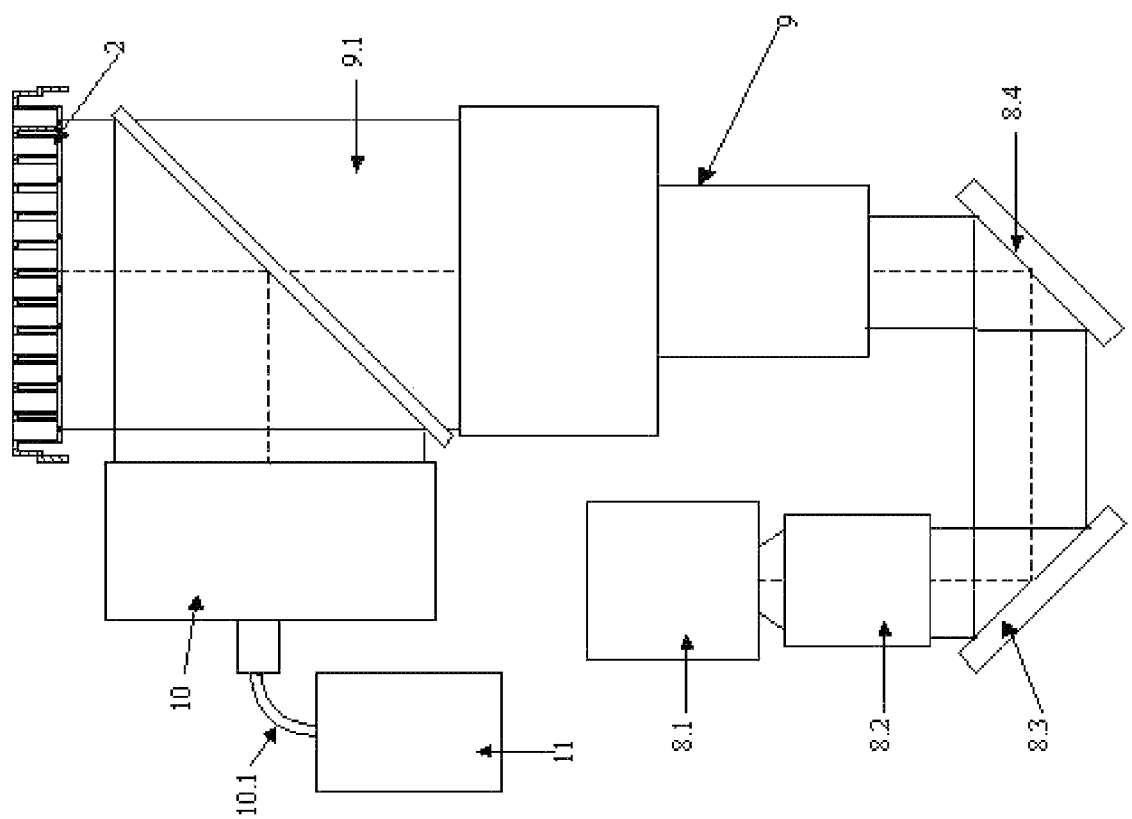
FIG. 2 shows a preferred embodiment of an analytical system according to the invention comprising a sensor platform 2, which is embodied as a microtiter plate, a beam splitter 9.1 and an illumination of the sensor platform 2 in an approximately perpendicular telecentrical manner as well as detection of the light emanating from the sensor platform in the direction of the reflection of the illuminating light.

FIG. 2 shows a preferred embodiment of an analytical system according to the invention. The illuminating unit 8 comprises a light source 8.1, an electro-optical unit 8.2 for generating an intensity distribution of the illuminating light, which is homogenous across the illuminating cross section. The electro-optical unit 8.2 preferably also comprises a telecentric optical illustration system. The light, the intensity of which is homogenized across the illuminating cross section, is subsequently guided in the illuminating light path via a deflection mirror 8.3 for the purpose of enabling a compact design, into the arrangement 8.4 identified as SLM for the temporally variable spatial light modulation. The use of "Digital Mirror Devices" DMD is advantageous for many applications, because the polarization characteristics of the light are barely influenced by means of the mirror surface. The configuration according to FIG. 2 uses a DMD by Texas Instruments Inc. (Plano, Tex., USA), for example. The approx. 13 µm×13 µm micro mirrors of this DMD can be switched back and forth individually in their position between +12° and −12°, wherein a speed of up to 16300 frames/sec can be attained with a size of the DMD of 1024×768 pixels (individual mirrors).

In the optical light path after the DMD (in the direction of the sensor platform), an optical module consisting of prisms (identified as "TIR-prism") can be used to allow for the light to pass in the direction of the illuminating optics 9 (ON state of the pixel of the illuminating light) or to block the light by means of total internal reflection (TIR) (OFF state of the pixel of the illuminating light). Light, which passes through the DMD as SML and an optional additional TIR prism is further directed to the sensor platform 2 by means of the illuminating optics 9. Preferably, the illuminating optics 9 comprises optical components, which act in a telecentric manner and which enable a good control of the angle of incidence on the sensor platform 2 and of the numerical aperture of the illuminating light bundle. Telecentric illuminating optics can comprise lens systems or mirrors, as described in U.S. Pat. No. 6,324,016.

The sensor platform can be illuminated under an angle of incidence of 0°, that is, parallel to the surface normal of the substantially planar sensor platform. In the case of an angle of incidence, which is clearly different from zero, additional provisions can be provided in the illuminating light path for corrections relating to the compensation of oblique light incidence according to Scheimpflug.

Figure 6:
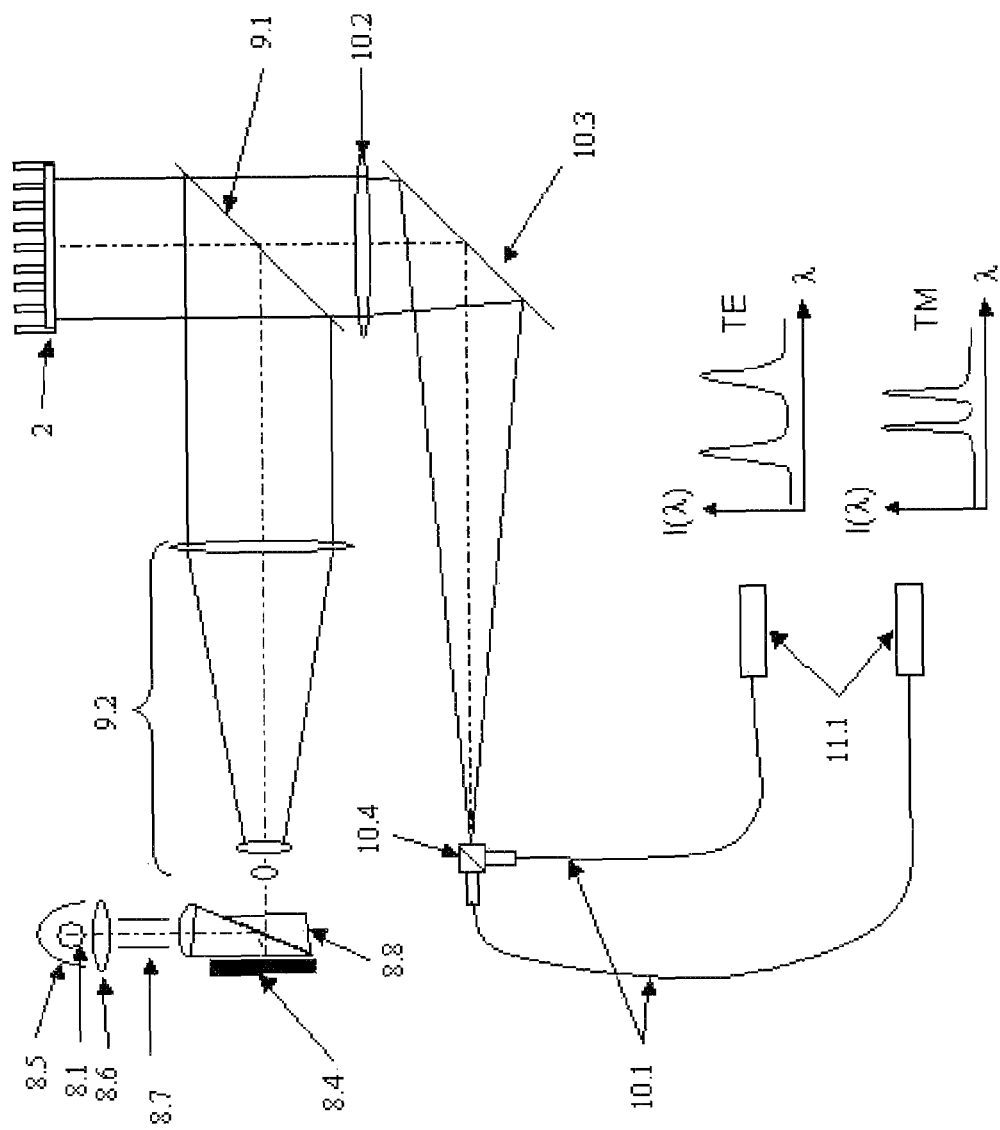
FIG. 6 shows a preferred embodiment of an analytical system according to the invention comprising a sensor platform 2, which is embodied as a microtiter plate, a beam splitter 9.1 and illumination of the sensor platform 2 in an approximately perpendicular manner as well as detection of the light emanating from the sensor platform in the direction of the reflection of the illuminating light for different polarizations by means of two spectrometers 11.1 as light analysis units.

Filters such as polarization filters, spatial filters and spectral filters can be used in the illuminating light path and/or in the detection light path in particular for improving the signal-to-noise and/or the signal-to-background ratio of the metering signals, which are to be generated by means of the analytical system. The simultaneous use of two different polarizations (TE and TM polarization) makes it possible to obtain additional information, as first described in U.S. Pat. No. 4,815,843 and later also in U.S. Pat. No. 5,442,169 as well as in Application US 2005/0070027. Variations in the optical index of refraction of the medium can be differentiated above the sensor platform and layer thickness variations on the surface of the sensor platform can be differentiated by means of the signals of thin-film waveguides, for example, comprising grids structured therein from the simultaneously or sequentially metered signals in response to TE and TM polarization. In order to meter both polarizations, the metered optical spectrum can be analyzed in that the spectrum to be expected for different polarizations is computed by means of mathematical models and is compared with the metered spectrum, which enables an assignment of the characteristic characteristics of the metered spectrum, such as "peaks", for example, to the different polarizations. The polarizations can also be detected separately, such as with the use of polarizing components, polarizers or polarizing beam splitters, in the illuminating system and/or in the detection system. The possibility of separating s-polarized and p-polarized light by means of a polarizing beam splitter and the subsequent coupling of the light separated after polarization into optical fibers for the subsequent separate detection of the spectra of the TE-polarized and TM-polarized light, is illustrated in FIG. 6. In a preferred embodiment of an analytical system according to the invention, a metering arrangement according to FIG. 8 from U.S. Pat. No. 4,815,843 is used, which is introduced herewith into this application together with the corresponding portion of the description.

For the detection of the light emanating from the sensor platform, a combination of a light collecting optics 10 and a detection unit 11 is preferably used, as is illustrated in the most general form in FIG. 1 for the detection in the direction rectified to the reflection and as is illustrated in FIG. 4 for the detection in transmission direction in the most general form.

Figure 5:
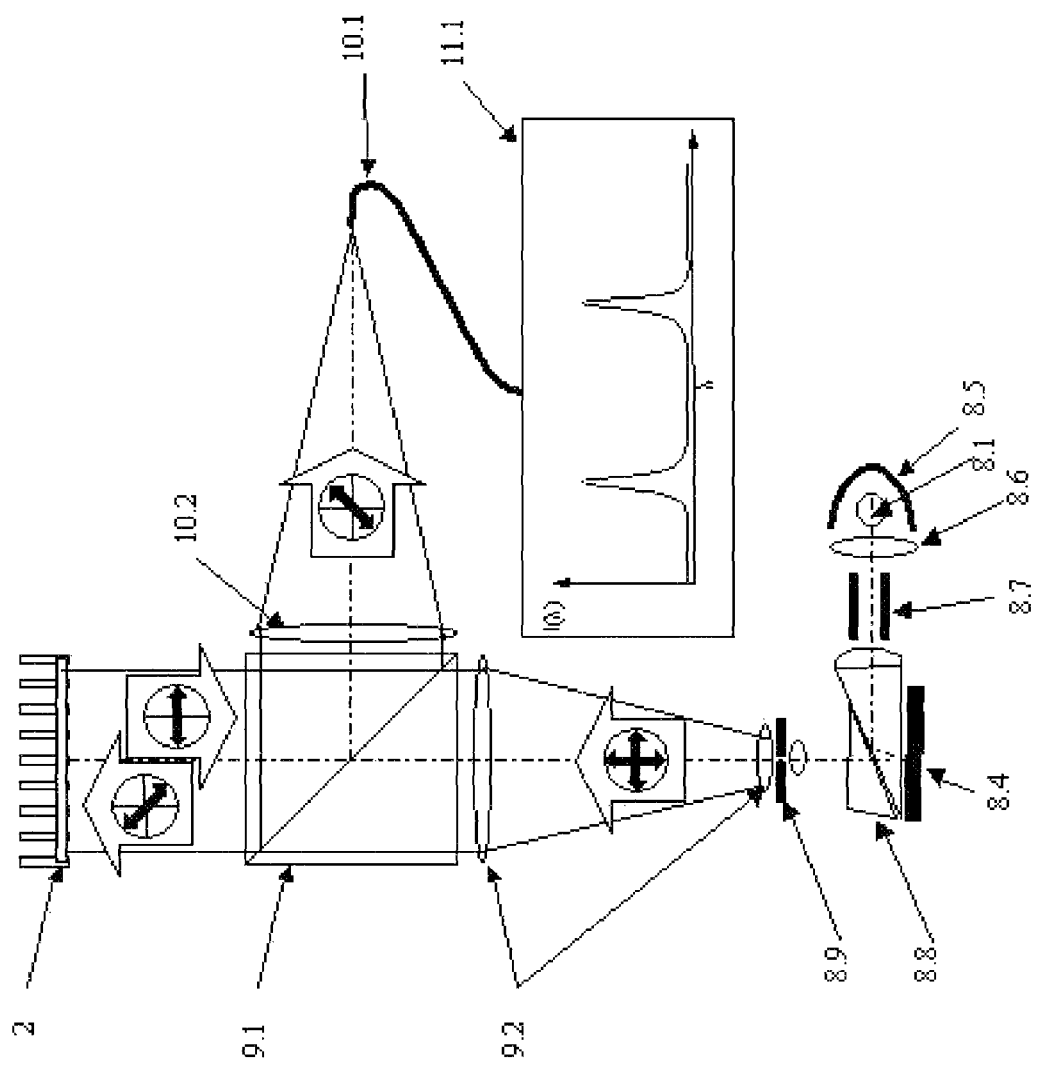
FIG. 5 shows a preferred embodiment of an analytical system according to the invention comprising a sensor platform 2, which is embodied as a microtiter plate, a beam splitter 9.1 and illumination of the sensor platform 2 in an approximately perpendicular manner as well as detection of the light emanating from the sensor platform in the direction of the reflection of the illuminating light by means of a spectrometer 11.1 as light analysis unit.

In response to small irradiation angles 6 and detection angles 7, a beam splitter 9.1 is preferably used for separating the irradiated illuminating light from the light emanating from the sensor platform and to direct the illuminating light under the suitable irradiation angle onto the sensor platform as well as to direct the light emanating from the sensor platform to the detection unit, as is illustrated in FIGS. 2, 5 and 6.

In a preferred embodiment of the analytical system according to the invention, as it is illustrated in FIG. 2, light emanating from the sensor platform 2 in reflection direction is focused from a light collecting optics 10, for example an optical tens, onto an end of an optical fiber 10.1 and is coupled into the fiber through this front surface of the fiber and is subsequently guided to the detection unit 11. Preferably, the detection unit 11 comprises a spectrometer, in which the collected light emanating from the sensor platform 2 can be analyzed in a spectral manner.

The angular distribution of the light, which is to be detected by the light collecting optics 10 and which emanates from the sensor platform 2, can be varied and determined by means of suitably selecting the optical characteristics, for example the numeral aperture, of the light collecting optics 10. Narrow angular ranges, that is, small angles of aperture of the light cone, which are formed by the light emanating from the sensor platform 2, are preferred for sensor platforms, which are based on refractive metering principles, that is, in particular for sensor platforms, which operate in a so-called label-free manner. In particular light beams comprising a narrow angle of aperture can be optimally coupled into an optical fiber in that the light bundle is focused onto an end surface of the fiber, which is arranged in the distance of the focal length of the light collecting optics 10, thus a collecting tens, e.g.

The spectral characteristics of the light emanating from the sensor platform can be used to obtain information relating to the surface condition, that is, in particular the surface configuration, of the sensor platform and thus also information relating to chemical, biochemical or biological processes, in particular bonding or adsorption or desorption processes on the surface of the sensor platform. The evaluation technologies and mathematical models required for doing so are disclosed in the afore-mentioned patents and patent applications and are also known to the person of skill in the art from his general expert knowledge and from pertinent textbooks. Known mathematical models are, for example, the "Rigorous Coupled Wave Analysis" (RCWA), which is often also referred to as "Fourier Modal Method" (FMM) and which is used and described in M. G. Moharam and T. K. Gaylord, "Diffraction analysis of dielectric surface-relief gratings", J. Opt Soc. Am., 72 (1997) 1385-1392 or in J. Turnen, "Diffraction theory of microrelief gratings" in Microoptics, H. P. Herzig, editor, Taylor & Francis Inc., (1997). Further mathematical models are the S- and R-matrix method, which is described in detail in Lifeng Li, "Formulation and comparison of two recursive matrix algorithms for modeling layered diffraction gratings", J. Opt Soc. Am. A, Vol. 13, 5, 1996 as well as the C-method, which is described in Lifeng Li, Jean Chandezon, Gerard Granet, Jean-Pierre Plumey, "Rigorous and efficient grating-analysis method made easy for optical engineers", Appl. Opt., 38 (1999) 304-313, the method identified as "Equivalent Source Method", which is described in A. V. Tischenko, M. Hamdoun and O. Parriaux, "Two-dimensional coupled mode equation for grating waveguide excitation by a focused beam", Opt. Quantum Electon. Special Issue on Workshop WTNM, Nottingham. 2001 as well as methods, which are described in R. H. Morf, "Exponentially convergent and numerically efficient solution for Maxwell's equations of lammelar gratings", J. Opt. Soc. Am. A, Vol. 12, 1043-1056, 1995. Said models, methods and processes and the descriptions thereof in the afore-mentioned publications are hereby completely introduced as components of the instant application.

A further preferred embodiment of the analytical system according to the invention is illustrated in FIG. 5. The optical components of the illuminating system and of the detection system largely correspond to those of the embodiment according to FIG. 2. The illuminating unit comprises a light source 8.1 and a mirror 8.5, which is embodied in the rear in the light path, which is preferably embodied as a parabolic mirror. The light emitted from the light source 8.1 is homogenized in that the light is focused onto the front side of a "light tunnel" or "light rod" 8.7 by means of a lens system 8.6. Due to multiple reflections within the "light tunnel" or "light rod" 8.7, the intensity distribution of the light at the outlets thereof is virtually homogenous and is directed through a prism system 8.8, preferably a TIR prism, onto a spatial light modulator 8.4 as SMM, preferably a Digital Mirror Device (DMD). A spatial filter 8.9 can be used in front of or behind the spatial light modulator 8.4 so as to impact the numerical aperture and the angular distribution of the light beams advancing in the direction of the sensor platform 2. A spatial filter substantially consists of an aperture stop, which is inserted into the light path. The light coming from the spatial filter 8.9 is substantially non-polarized, which is illustrated in FIG. 5 by means to two filled arrows, which are perpendicular to one another, according to the light polarization directions within a circle, while the main expansion direction of the light is illustrated by means of an unfilled arrow, which encompasses the circle.

The light is collimated by means of a lens system 9.2 and is directed onto a beam splitter 9.1, preferably a polarizing beam splitter, which preferably transmits only one polarization direction. The sensor platform 2, preferably an evanescent field sensor platform comprising grid structures, which encompass a period type of the grid lines, which is embodied in one or two dimensions, is illuminated by means of the light, which is preferably polarized after the beam splitter 9.1. The grid lines of the sensor platform are aligned in an angle of preferably 45° to the polarization direction, which is indicated by means of the individual filled double arrow, which in the illuminating light path symbolizes the polarization of the illuminating light in front of the sensor platform. After the interaction with the grid-waveguide structure, the light emanating and reflected from the sensor plate, respectively, is polarized in a transverse electric (TE) and/or transverse magnetic (TM) manner and encompasses a polarization direction (indicated by the horizontal double arrow in the drawing plane), which is turned by 45° as compared to the illuminating light and will be identified below as light emanating from the sensor platform or as "signal light". The polarization direction and the expansion direction of the light are in each case illustrated by means of the arrows in FIG. 5.

Light, which was not subjected to an interaction, for example by means of reflection or coupling into the grid-waveguide structure, guidance in the waveguide and subsequent uncoupling, will be identified below as "diffused light". The diffused light generally has the same polarization as the irradiated illuminating light.

The light portions, which have been subjected to an interaction with the sensor platform, that is, in the case of a sensor platform based on a grid-waveguide structure, will be identified in this application as "light emanating from the sensor platform".

The polarizing beam splitter 9.1 directs the light emanating from the sensor platform onto a lens system 10.2 as a component of the light collecting optics. Only the "signal light", the polarization direction of which was varied by means of an interaction with the sensor platform, is directed to the lens system 10.2, while the "diffused light", the polarization direction of which is substantially unvaried, is transmitted by means of the polarizing beam splitter 9.1. The "signal light" is thus separated from the "diffused light", which can lead to an improvement of the signal-to-noise ratio. This configuration is often also identified as system comprising "crossed polarizers". The "signal light" is directed into an optical fiber 10.1 by means of a lens system 10.2 and is guided to a light analysis unit 11.1, for example a spectrometer, as a component of a detection unit. The figure illustrates schematically a typical spectral curve (measured intensity $I(\lambda)$ as function of the wavelength $\lambda$), as it can develop at a grid-waveguide structure by means of reflection.

A further preferred embodiment of an analytical system according to the invention is illustrated in FIG. 6. The optical components of the illuminating system and of the detection system largely correspond to those of the embodiments according to FIGS. 2 and 5. The non-polarized light emanating from the lens system 9.2 is directed to the sensor platform 2 by means of a beam splitter 9.1. The light emanating from and reflected by the sensor platform 2, respectively, is transmitted by means of the beam splitter 9.1 and is directed onto a polarizing beam splitter 10.4 by means of a lens system 10.2 and by means of a deflection mirror 10.3, the use of which allows for the realization of a more compact design. The polarizing beam splitter 10.4 separates the two polarization directions of the light arriving thereon. The two polarization directions are separately coupled into optical fibers 10.1, which guide the light to the light analysis unit 11.1, for example to a plurality of spectrometers, for detecting the spectra for different polarizations. The figure illustrates schematically typical spectral curves, as they can develop at a grid-waveguide structure by means of reflection for TE and TM polarization.

Figure 7:
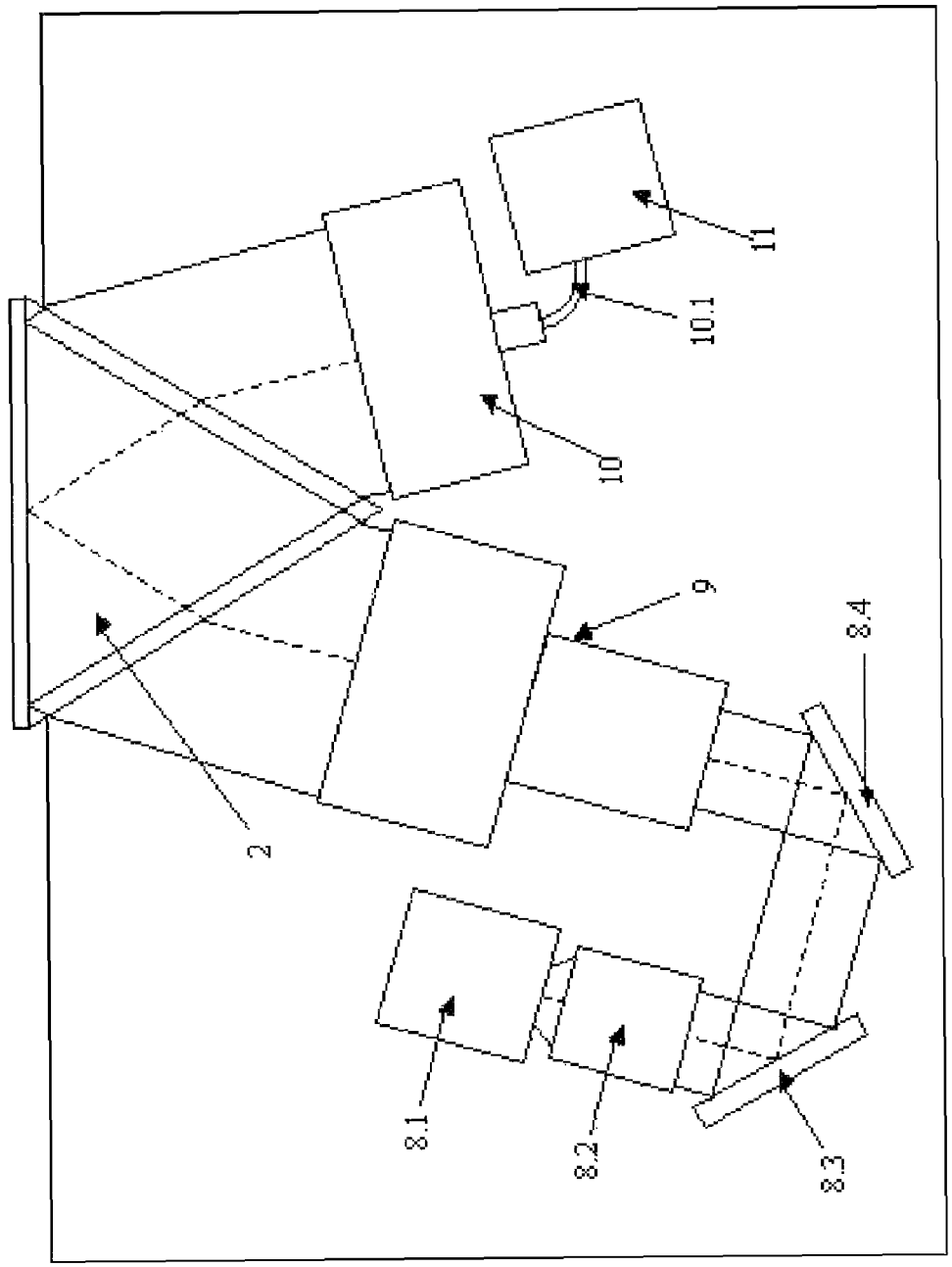
FIG. 7 shows an embodiment of a an analytical system according to the invention having a similar design as that of FIG. 2 comprising a sensor platform 2, which is embodied as a prism for generating internal total reflection or as "resonant mirror".

A further preferred embodiment of an analytical system according to the invention is illustrated in FIG. 7. The optical components of the illuminating system and of the detection system largely correspond to those of the embodiment according to FIG. 2. The embodiment according to FIG. 7 is characterized in that a prism or a "resonant mirror" is used herein as sensor platform 2 for generating internal total reflection.

Figure 8:
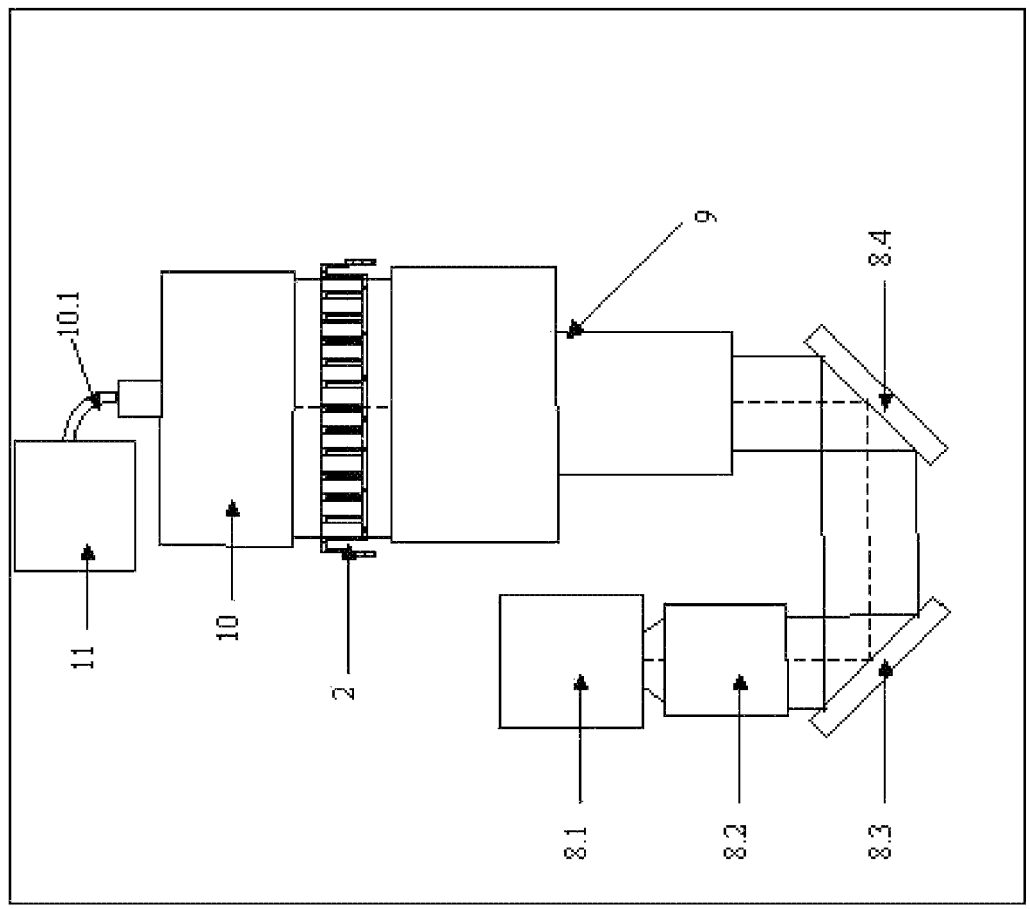
FIG. 8 shows an embodiment of an analytical system according to the invention, which is similar to that of FIG. 2, but with detection of the light emanating from the sensor platform 2 in transmission direction.

FIG. 8 shows a further preferred embodiment of an analytical system according to the invention, where the sensor platform 2 is embodied as a microtiter plate and as the components thereof, respectively. Furthermore, the irradiation of the illuminating light and the detection of the light emanating from the sensor platform are carried out in this embodiment on opposite sides of the sensor platform, thus in a transmission light or transmitted light arrangement.

A further embodiment of an analytical system according to the invention is characterized in that the illuminating system comprises two or more arrangements for the temporally rapidly variable spatial light modulation. Advantageously, such an embodiment is characterized by an increase of the spatial resolution of the illuminating pattern, which is to be generated on the sensor platform and/or by a further possible increase of the reading speed of the light signals emanating from the sensor platform, in response to the correlation of the detection steps comprising the light modulation by the two or plurality of SLMs. This embodiment is particularly preferred in combination with sensor platforms, which are embodied as microtiter plates.

Figure 9B:
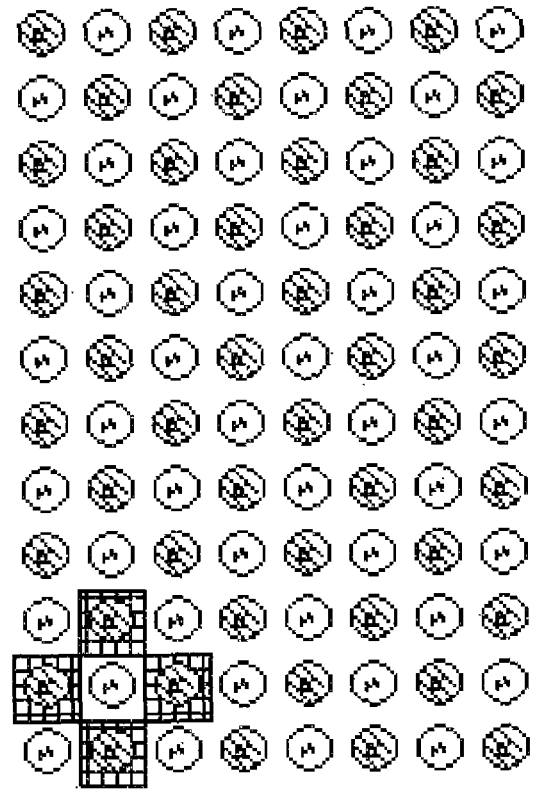
FIG. 9 uses the example of a microtiter plate as a sensor platform to show possible variations of the illuminating pattern, which can be generated on the sensor platform by means of a spatial light modulator SLM, a) by means of illuminating a single well of the microtiter plate, characterized with "S" and surrounded by a shaded square; b) simultaneous illumination (identified by a shaded cross) of four surrounding wells (identified with "R").
Figure 9A:
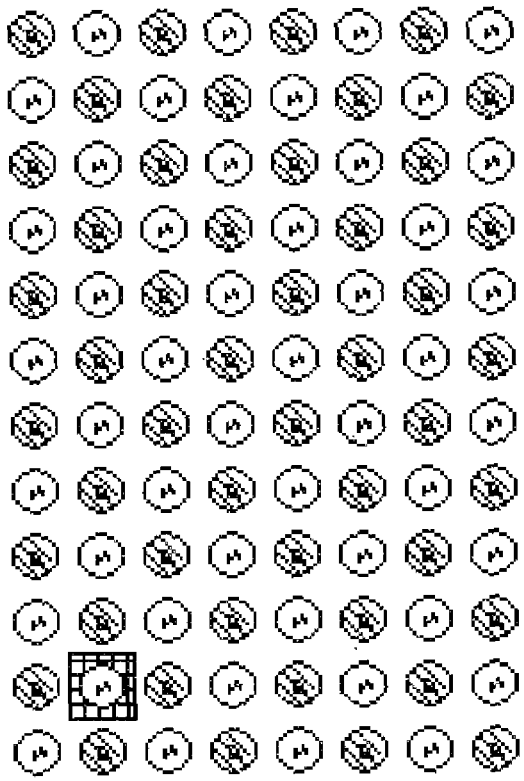

Using the example of a microtiter plate comprising 96 wells, FIGS. 9a and 9b show possible variations of the illuminating pattern generated on the sensor platform, wherein said illuminating pattern can be optimally adapted to the geometry of the metering ranges on the sensor platform. FIG. 9a illustrates the illumination of an individual metering range, which is equivalent herein to an individual well of the microtiting plate. The illuminating pattern is illustrated herein by means of a shaded square around a metering range (well) of the sensor platform identified with "S". FIG. 9b illustrates the simultaneous illumination (shaded cross) of 4 surrounding metering ranges (wells), which are used, for example, for collecting reference metering and which are identified with "R".

Figure 10C:
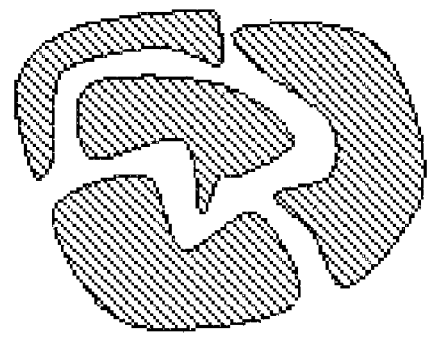
FIG. 10 shows further illuminating patterns having a different geometry, which can be generated on the sensor platform: a) illumination of metering ranges in a hexagonal pattern; b) illuminating pattern consisting of concentric circular rings; c) an illuminating pattern comprising arbitrary irregular geometries, as it can correspond to the specific illumination of biological cells located on the sensor platform, for example.
Figure 10B:
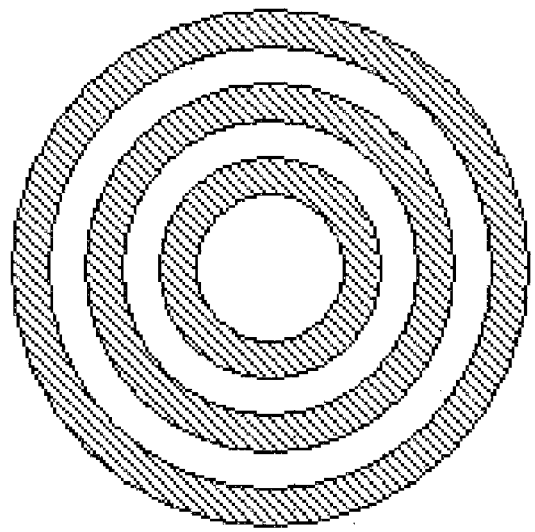
Figure 10A:
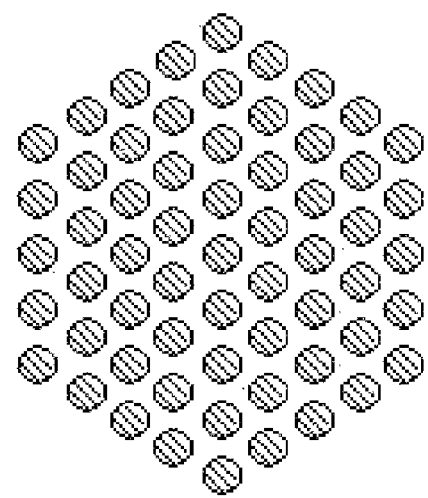

FIGS. 10a-10c illustrate how the illuminating pattern, which is to be generated on the sensor platform, can be adapted to the most varied geometries. FIG. 10a illustrated the illumination of a plurality of metering ranges in a hexagonal pattern. FIG. 10b shows the illumination of metering ranges, which are arranged in concentric circular rings. FIG. 10c illustrates an illuminating pattern comprising an arbitrary irregular geometry, as it can correspond, for example, to the specific illumination of the biological cells located on the sensor platform. The generated illuminating pattern can thereby be changed within a very short period of time in each case by means of discretely switching the individual elements of the SLM and can be adapted to the variations of the geometry of the metering ranges, for example.

A further object of the instant invention is a method for generating and measuring optical signals and/or the variations thereof from metering ranges, which are arranged in a one-dimensional or two-dimensional array on a substantially optically transparent sensor platform, while using an analytical system according to one of the below-described embodiments, at least comprising an optical system comprising an illuminating system for illuminating metering ranges on the sensor platform comprising an arrangement identified as "SLM" for the temporally rapidly variable spatial light modulation as well as a detection system comprising at least one detection unit for detecting signals from the metering ranges on the sensor platform, in the direction of the transmission or reflection of the illuminating light in a spectral range, which comprises the spectral range of the illuminating light, and a sensor platform, which can be inserted into the optical system, comprising metering ranges, which are arranged thereon in a one-dimensional or a two-dimensional array, characterized in that in the operating state, illuminating patterns of a freely selectable and rapidly variable geometry, which can be determined by the settings of the SLM, can be generated on the sensor platform from an illuminating light, which enters into this SLM and which comprises a substantially homogenous intensity distribution in the cross section of the illuminating light at right angles to its direction of expansion.

Preferred is thereby a method, which is characterized in that a brightness distribution of the signals is measured by means of the detection system comprising at least one detection unit, and that this brightness distribution is analyzed independent on the metered absolute signal intensities.

Particularly preferred is thereby an embodiment of the method according to the invention, which is characterized in that the optical signals and/or the variations thereof are generated from discrete metering ranges by means of one or a plurality of bonding or adsorption results between one or a plurality of analytes in one or a plurality of specimens and specific identification elements for said analytes in or on said metering ranges, wherein the specimens and the identification elements for the analytes on the metering ranges, which are to be detected in the specimens, are brought into contact with one another and in that a simultaneous qualitative and/or quantitative detection of a plurality of analytes in one or a plurality of specimens and/or of one or a plurality of analytes in a plurality of specimens is made possible from these optical signals and/or the variations thereof.

A further object of the instant invention is the use of an analytical system according to one of the afore-mentioned embodiments and/or a method according to one of the afore-mentioned embodiments for quantitative and/or qualitative analyses for determining chemical, biochemical or biological analytes in screening methods in pharmaceutical research, the combinatory chemistry, the clinical and preclinical development, for real time bonding studies and for determining kinetic parameters in affinity screening and in research, for qualitative and quantitative analyte determinations, in particular for the DNA and RNA analysis and for the determination of genomic or proteomic differences in the genome, such as, for example, individual nucleotide polymorphisms, for metering protein-DNA interactions, for determining control mechanisms for the m-RNA expression and for the protein(bio)synthesis, for the preparation of toxicity studies as well as for the determination of expression profiles, in particular for the determination of biological and chemical marker substances, such as mRNA, proteins, peptides or low-molecular organic (messenger) substances, as well as for detecting antibodies, antigens, pathogens or bacteria in the pharmaceutical product research and development, in human and veterinary diagnostics, the agrochemical product research and development, the symptomatic and presymptomatic plant diagnostic, for patient stratification in the pharmaceutical product development and for the therapeutic drug selection, for detecting pathogens, toxic substances and viruses, in particular of salmonella, prions, viruses and bacteria, in particular in the analysis of food and the environment.

The instant invention will be defined in more detail in the following examples without limiting the commonality.

EXAMPLES

Example 1

Figure 12:
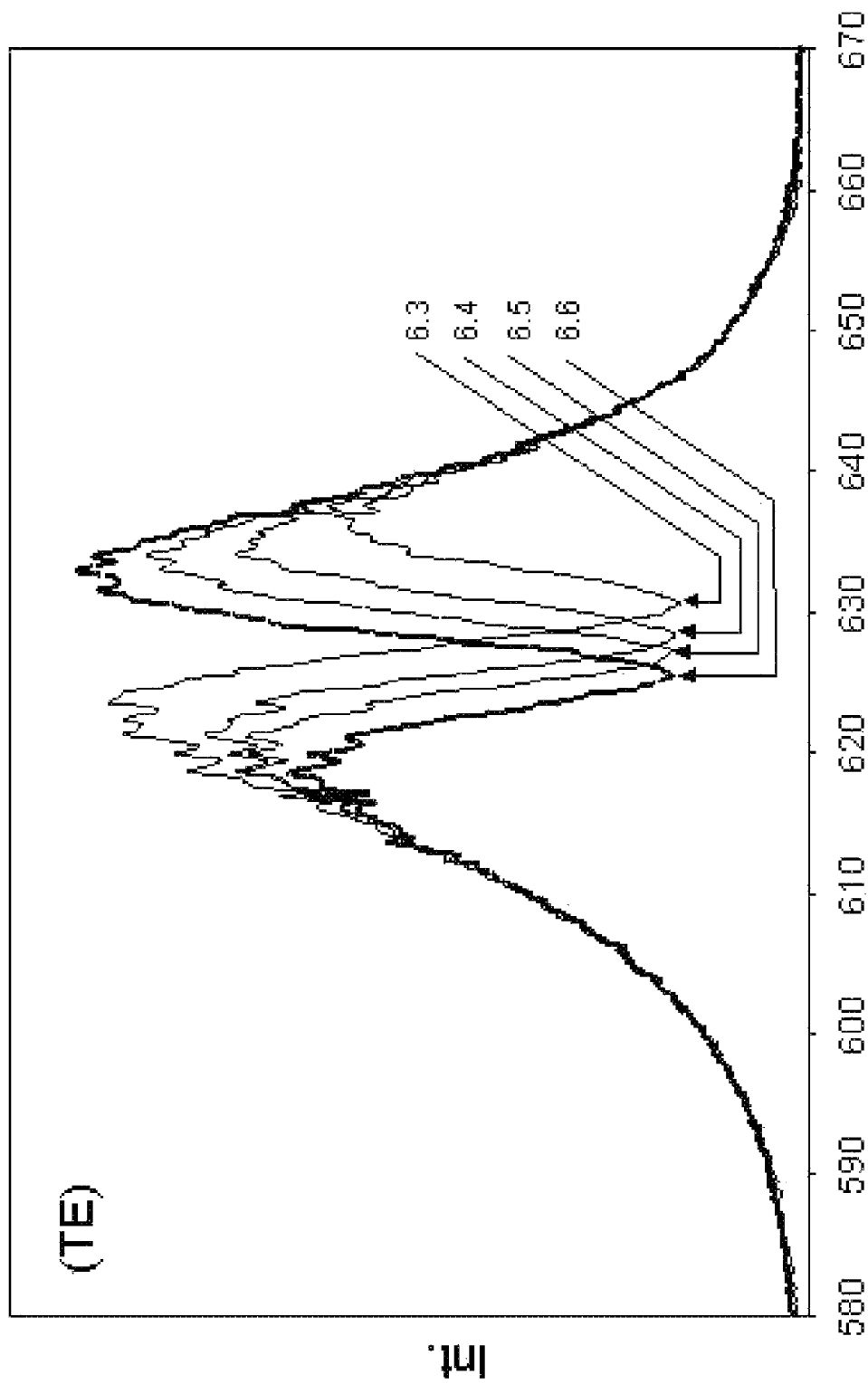
FIG. 12 shows the spectrums of the TE-polarized illuminating light of the red LED from FIG. 11 absorbed in transmission for four variably adjusted angles of incidence 6.3, 6.4, 6.5 and 6.6 of the illuminating light onto the sensor platform.

The assembly of the analytical system corresponds to the embodiment according to FIG. 4, that is, to the arrangement of the illuminating system and of the detection system on opposite sides of the sensor platform and detection of the transmitted light portion. According to a preferred embodiment of such an arrangement, the illuminating system 1 comprises a commercial projection system comprising light-emitting diodes (LEDs) as light sources. A projection system of type FF1 (Toshiba, Taiwan), for example, is suitable for this purpose. FIG. 12 shows the emission spectrum of this projector in response to a simultaneous operation of all three LED light sources. The used blue, green and red LEDs have central emission wavelengths of 460 nm, 520 nm and 627 nm, respectively, and a spectral emission bandwidth of typically 20 nm to 40 nm. The following examples mainly use the red light source, wherein it goes without saying that light sources of other emission spectrums, for example comprising a blue or green emission, can also be used. The light from the LEDs is homogenized by means of a "light tunnel" and is directed to a Digital Mirror Device (DMD) as SLM. The light reflected by the DMD is directed through a first lens system, which is included in the projection system. The light coming from the projector is imaged onto the sensor platform, which has a distance of approximately 1 m from the projector, by means of an additional lens (focal width f=500 mm) as part of the illuminating optics 9. The illuminating unit comprises a polarizer in the illuminating light path for the purpose of controlling and determining, respectively, the polarization of the illuminating light.

The optical sensor platform comprises a thin-film waveguide comprising a grid structure structured therein, that is, a structure, as it is also known under the identification "resonant grid structure". Said grid structure comprises a planar glass substrate as support comprising an index of refraction of 1.5 at 633 nm and comprising two large-surface parallel surfaces at a distance of 1 mm as thickness of the support, an optical grid being structured with a period of 360 nm in the one of said two mentioned surfaces. Preferably, this grid is pronounced as a surface relief grid comprising bars and grooves, which are parallel to one another, and having the same bar width in each case and the same groove width, respectively, wherein the distance between two succeeding bars and grooves, respectively, is identified as the grid period. The grid can be embodied holohedrally across an entire surface of the glass substrate. The grid is covered with a substantially optical transparent layer comprising an index of refraction of 2.1 at 633 nm and a thickness of 150 nm as waveguiding layer.

As it is known to the person of skill in the art, there is one discrete resonance angle in each case for coupling light into the high-refracting waveguiding layer of such a grid waveguiding layer for light coupling in forward direction of the light expansion in the waveguide and one angle of resonance for coupling light in reverse direction of the light expansion in the waveguide, in response to irradiation of illuminating light of a discrete wavelength and of a certain polarization. For example, the angles of resonance for light coupling of TM- and TE-polarized light comprising a 626 nm wavelength can differ by a range of 10°. For illuminating light of a different wavelength, the angles of resonance are again different. In response to the irradiation of illuminating angle under a fixed irradiation angle, but with a certain spectral width of 1 nm to 10 nm, for example, the wavelength of the light portion, for which the resonance condition for the light coupling is fulfilled with the predetermined irradiation angle, is thus also identified as the "resonance wavelength".

In response to a suitable selection of the spectral width of the light source and of the physical characteristics (in particular layer thickness, grid period and grid depth) of the "resonant grid structure", it is possible to simultaneously fulfill the resonance conditions for light coupling in reverse direction as well as in forward direction of the light expansion in the waveguide. The center of the two resonances corresponds to the auto-collimation angle, which corresponds to the plumb line to the surface plane of the sensor platform. In addition to the determination of the metered variable, the orientation of the sensor platform can also be determined in the region of the metering range.

When suitably selecting the spectral width of the light source and the characteristics of the "resonant grid structure", the resonance conditions for light coupling can furthermore be fulfilled simultaneously for both polarization directions, that is, for TE- and TM-polarization. As will be described below in more detail, the thickness and the index of refraction of a layer, e.g. an adhesion-promoting layer, which is applied to the surface of the sensor platform, a complete or partial, that is, broken layer of detection elements can be simultaneously determined therewith for the detection of analytes or from bonded analyte compounds.

It goes without saying that the simultaneous fulfilling of the resonance conditions can also be realized in combination for the light coupling for both expansion directions as well as for both polarization directions.

Variations of the effective index of refraction can be determined from variations of the angle of resonance and of the resonance wavelength. Said variations are caused, for example, by molecular adsorption or desorption processes on the surface of the sensor platform and by corresponding variations of the (macroscopic) index of refraction on this surface. Due to the known dependency of the index of refraction on the layer and light parameters, for example absolute or relative variations of the area density on the surface of the sensor platform can be determined from these variations of the effective index of refraction and from the angle of resonance or the resonance wavelength as coupling parameters of the sensor platform. Provided that a calibration of these variations comprising known area densities (e.g. comprising complete or partial monolayers of surface-adsorbing molecules having known molecular weight) is carried out or is present, absolute values of the surface density can also be determined. In particular when the density of the surface density is known, conclusions can also be drawn, for example, from the level of the signal variations with reference to the orientation of the adsorbed molecules in the case of surface-adsorbing molecules, which are not spherically symmetric. This even allows for conclusions relating to the nature of the corresponding chemical, biochemical or biological adsorption or bonding process. Vice versa, corresponding variations of the coupling parameters can be simulated for simulated adsorption processes and the models for these simulated adsorption processes can then be examined by means of real metering variables.

In response to a simultaneous metering for two different polarizations, mathematical models enable a determination of the index of refraction and of the thickness of a layer accumulated on the surface. This additional information allows for further conclusions. It can thus be determined, for example, whether molecules have accumulated on the surface as a dense monolayer or whether they have accumulated loosely and in a plurality of layers. Simplified conclusions relating to the orientation of molecules, which are not spherically symmetric, can also be drawn in this case, because different orientations of the molecules on the surface, for example for "lying" molecules and for "standing" molecules lead to different optical characteristics of the sensor layer, in particular to different indexes of refraction and layer thicknesses in response to the same area density.

In accordance with the embodiment according to the configuration of FIG. 4, the detection unit is oriented in transmission direction along the optical axis of the illuminating light generated by the illuminating unit, wherein in this case the detection angle 7 corresponds to the angle of incidence 6 of the illuminating light on the sensor platform. A lens having a focal width of 500 mm is used in this example as the light collecting optics 10, whereby the light is focused onto the entry front face of an optical fiber, from where the light portion, which is coupled into the fiber in this manner and which is conveyed therein, is guided into a spectrometer for the purpose of a further spectral analysis. The lens is thereby arranged in each case at a distance of approximately 500 mm between the sensor platform and the optical fiber.

Figure 13:
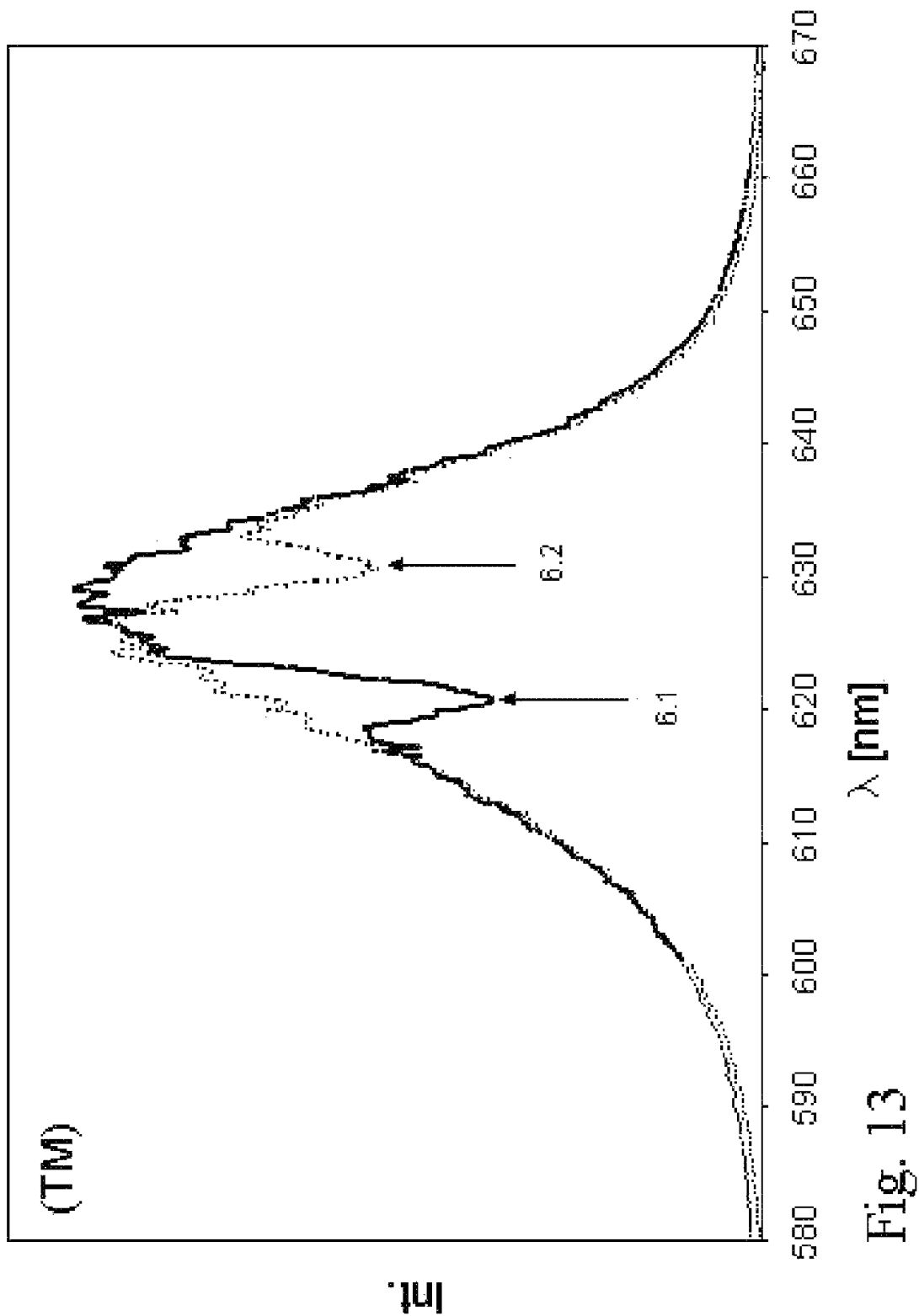
FIG. 13 shows the spectrums of the TM-polarized illuminating light of the red LED from FIG. 11 absorbed in transmission for two variably adjusted angles of incidence 6.1 and 6.2 of the illuminating light onto the sensor platform.

FIG. 12 shows the spectra of the TE-polarized illuminating light of the red LED absorbed in transmission for four differently set angles of incidence 6.3, 6.4, 6.5 and 6.6 of the illuminating light onto the sensor platform. In response to the resonance wavelength for the light coupling, which corresponds in each case to the respective angle of incidence, the spectrum of the transmitted light encompasses a minimum. With known physical parameters of the sensor platform, the position, width and depth allow for conclusions relating to the effective index of refraction or relating to adsorption or desorption processes on the sensor platform. Corresponding spectra for TM-polarized illuminating light with two different angles of incidence 6.1 and 6.2 are illustrated in FIG. 13, wherein the transmission minima for the respective resonance wavelengths are less pronounced herein.

Example 2

Figure 3:
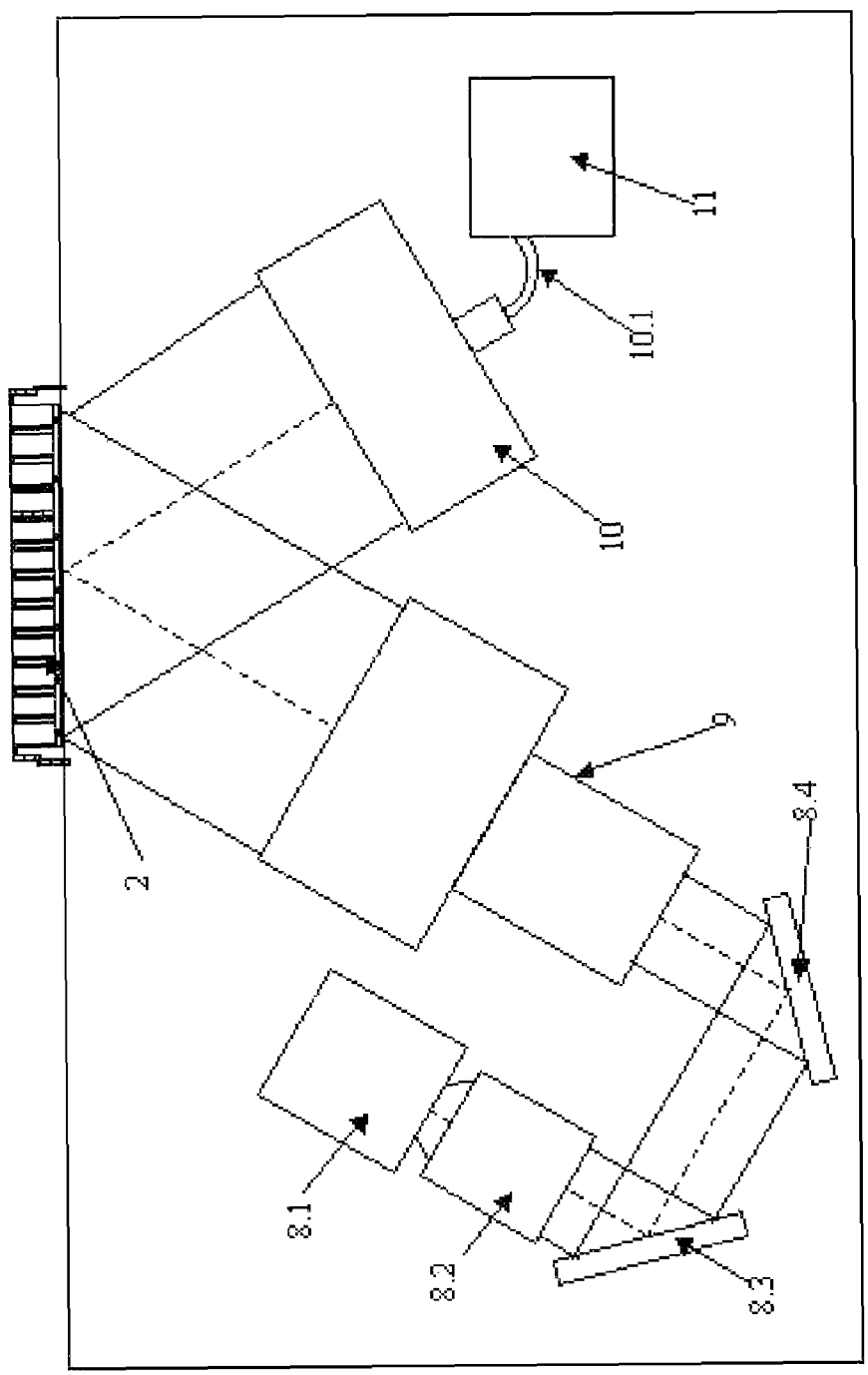
FIG. 3 shows an embodiment of an analytical system as in FIG. 2 according to the invention, which is similar with reference to the used electro-optical components, except for the beam splitter, but with irradiation of the illuminating light and detection of the light emanating from the sensor platform 2 under an angle, which clearly differs from the perpendicular, that is, from the oblique angle.
Figure 11:
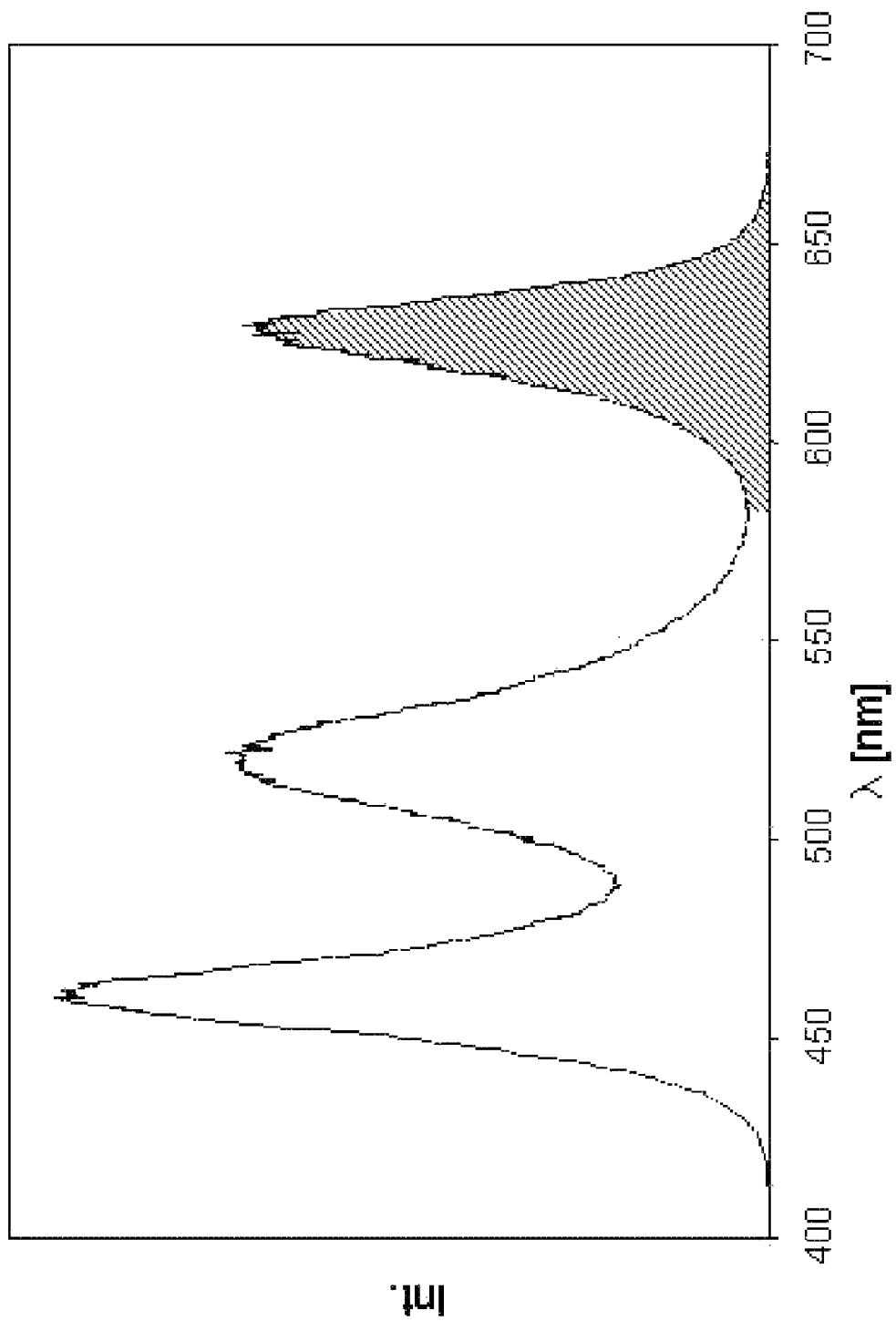
FIG. 11 shows the emission spectrum of a projection system used for examples 1 and 2 comprising three light-emitting diodes (LEDs) as light sources, comprising central emission wavelengths 460 nm (blue), 520 nm (green) and 627 nm (red), wherein the spectral emission width of the LEDs is only 20 nm to 40 nm in each case.

The assembly of the analytical system corresponds to the embodiment according to FIG. 3, that is, to the arrangement of the illuminating system and of the detection system on the same side of the sensor platform and detection in the direction of the reflected light portion. According to a preferred embodiment of such an arrangement, the illuminating system 1 comprises a commercial projection system comprising light-emitting diodes (LEDs) as light courses. A projection system of type FF1 (Toshiba, Taiwan), for example, is suitable for this purpose. FIG. 11 shows the emission spectrum of this projection system in response to a simultaneous operation of all three LED light sources. The used blue, green and red LEDs have central emission wavelengths of 460 nm, 520 mm and 627 nm, respectively, and a spectral emission bandwidth of typically 20 nm to 40 nm. The light of the LEDs is homogenized by means of a "light tunnel" and is directed onto a Digital Mirror Device (DMD) as SLM 4. The light reflected by the DMD is directed through a first lens system, which is included in the projection system.

The light coming from the projector is imaged onto the sensor platform, which has a distance of approximately 1 m from the projector, by means of an additional lens (focal width f=500 mm) as part of the illuminating optics 9. The illuminating unit comprises a polarizer in the illuminating light path for the purpose of controlling and determining, respectively, the polarization of the illuminating light.

The optical sensor platform comprises a thin-film waveguide comprising a grid structure structured therein, that is, a structure, as it is also known under the identification "resonant grid structure". Said grid structure comprises a planar glass substrate as support comprising an index of refraction of 1.5 at 633 nm and comprising two large-surface parallel surfaces at a distance of 1 mm as thickness of the support, an optical grid with a period of 360 nm being structured in the one of said two mentioned surfaces. Preferably, this grid is pronounced as a surface relief grid comprising bars and grooves, which are parallel to one another and having the same bar width in each case and the same groove width, respectively, wherein the distance between two succeeding bars and grooves, respectively, is identified as the grid period. The grid can be embodied holohedrally across an entire surface of the glass substrate. The grid is covered with a substantially optical transparent layer comprising an index of refraction of 2.1 at 633 nm and a thickness of 150 nm as waveguiding layer.

According to the embodiment according to the configuration of FIG. 3, the detection unit is oriented in the direction of reflection along the optical axis of the illuminating light generated by the illuminating unit, wherein in this case the detection angle 7 corresponds to the angle of incidence 6 of the illuminating light on the sensor platform according to amount, but having the opposite algebraic sign. A lens having a focal width of 500 mm is used in this example as the light collecting optics 10, whereby the light is focused onto the entry front face of an optical fiber, from where the light portion, which is coupled into the fiber in this manner and which is conveyed therein, is guided into a spectrometer for the purpose of a further spectral analysis. The lens is thereby arranged in each case at a distance of approximately 500 mm between the sensor platform and the optical fiber.

Figure 14:
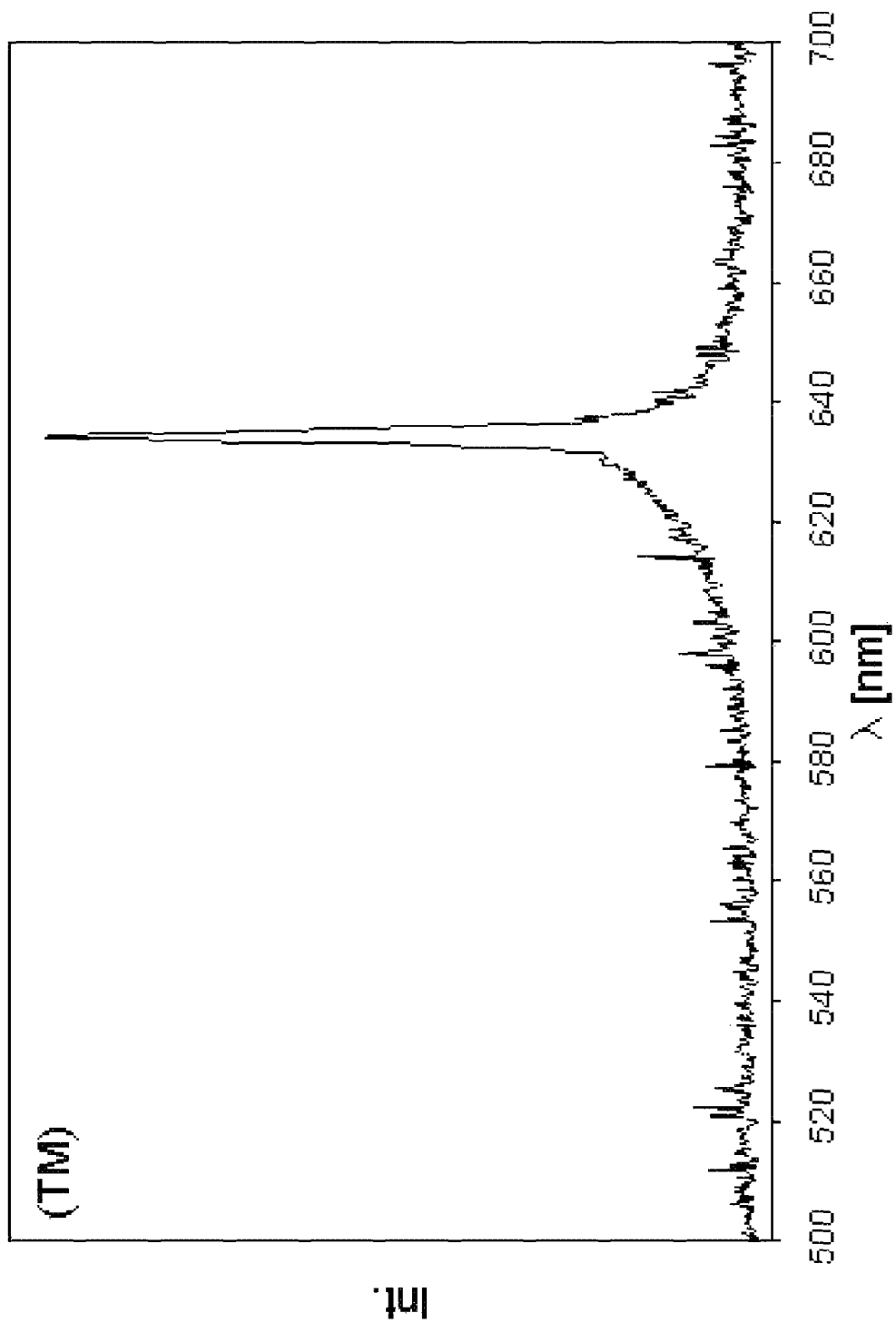
FIG. 14 shows the spectrum of the TM-polarized illuminating light of the red LED from FIG. 11 absorbed in reflection direction for an individually adjusted angle of incidence of the illuminating light onto the sensor platform.

FIG. 14 shows the spectrum of the TM-polarized illuminating light of the red LED absorbed in reflection direction for an individually adjusted angle of incidence of the illuminating light onto the sensor platform. In response to the resonance wavelength for the light coupling, which corresponds to this angle of incidence, the spectrum has a sharp maximum in reflection direction. With known physical parameters of the sensor platform, the position, width and depth allow for conclusions relating to the effective index of refraction or relating to adsorption or desorption processes on the sensor platform.

LIST OF REFERENCE NUMERALS

The following list of reference numerals is part of the disclosure of this patent application

1: illuminating system
2: sensor platform
3: detection system
4: illuminating light
5: light emanating from the sensor platform
6; 6.1; 6.2; 6.3; 6.4; 6.5; 6.6: angle of incidence on the sensor platform
7: detection angle
8: illuminating unit 8.1: light source
8.2: electro-optical unit for generating a distribution of the illuminating light, which is homogenous across the illuminating cross section
8.3: deflection mirror
8.4: arrangement for the temporally rapidly variable light modulation (SLM)
8.5: mirror
8.6: lens system
8.7: "light tunnel" or "light rod"
8.8: prism system
8.9: spatial filter
9: illuminating optics
9.1: beam splitter
9.2: lens system
10: light collecting optics
10.1: optical fiber
10.2: lens system
10.3: deflection mirror
11: detection unit
11.1: light analysis unit
11.2: polarizing beam splitter
12: specimen, test, calibrating or reference provisions fed to the sensor platform in liquid or gaseous form
12': specimen, test, calibrating or reference provisions discharged from the sensor platform in liquid or gaseous form

What is claimed is:

1. An analytical system for generating and metering optical signals and/or the variations thereof from metering ranges, which are arranged in a one-dimensional or two-dimensional array on a substantially optically transparent sensor platform, at least comprising
    an optical system comprising an illuminating system for illuminating metering ranges on the sensor platform and a detection system comprising at least one detection unit for detecting signals from the metering ranges on the sensor platform, in the direction of the transmission or reflection of the illuminating light in a spectral range, which comprises the spectral range of the illuminating light, and
    a sensor platform, which can be inserted into the optical system, comprising metering ranges, which are arranged thereon in a one-dimensional or a two-dimensional array,
    characterized in that the illuminating system comprises an arrangement identified as "SLM" for the temporally rapidly variable spatial light modulation, by means of which in the operating state, illuminating patterns of a freely selectable and rapidly variable geometry, which can be determined by the settings of the SLM, can be generated on the sensor platform from an illuminating light, which enters into this SLM and which comprises a substantially homogenous intensity distribution in the cross section of the illuminating light at right angles to its direction of expansion.

2. An analytical system according to claim 1, characterized in that in a one-dimensional or two-dimensional arrangement, the sensor platform preferably comprises more than 50, particularly preferably more than 500, even more preferably more than 50000 metering ranges.

3. The analytical system according to claim 1, characterized in that in a one-dimensional or multi-layer system, the sensor platform comprises a material from the group, which is formed forms from substantially optically transparent glasses, plastics and ceramics, wherein layers of these materials can optionally be provided with additional coatings.

4. The analytical system according to claim 1, characterized in that the sensor platform is embodied as an evanescent field sensor platform.

5. The analytical system according to claim 4, characterized in that the sensor platform is chosen from the group of prisms for generating internal total reflection, self-supporting optical waveguides, optical thin-film waveguides, thin-film waveguides comprising grids structured therein for the light coupling and/or light uncoupling, resonant grid structures as well as "resonant mirrors".

6. The analytical system according to claim 1, characterized in that the sensor platform has the basic dimensions of a microtiting plate or is embodied as a component of a microtiting plate.

7. The analytical system according to claim 1, characterized in that the arrangement for the temporally variable spatial light modulation is chosen from the group of "Digital Mirror Devices" DMD, liquid crystal displays LCD, "Liquid Crystal on Silicon Silicon" LCOS microdisplays and mechanically movable masks comprising light-permeable and light-blocking areas.

8. The analytical system according to claim 7, characterized in that the arrangement for the temporally variable spatial light modulation comprises a plurality of individual elements in a one-dimensional or two-dimensional arrangement, which can be switched discretely for the transmission to the sensor platform or for blocking the illuminating light, wherein a metering range of more than one of said individual elements is illuminated.

9. The analytical system according to claim 8, characterized in that the arrangement for the temporally variable spatial light modulation comprises a plurality of individual elements in a two-dimensional arrangement, which can be switched discretely for the transmission to the sensor platform or for blocking the illuminating light, with preferably more than 100×100 discretely switchable individual elements.

10. The analytical system according to claim 8, characterized in that an individual element of the arrangement for the temporally rapidly variable spatial light modulation encompasses a response time of less than 20 msec for changing between positions or settings for transmitting the illuminating light to the sensor platform or for blocking the illuminating light.

11. The analytical system according to claim 1, characterized in that the arrangement for the temporally rapidly variable spatial light modulation enables the generation of rapidly variable illuminating patterns on the sensor platform, whereby objects comprising a geometry, which varies temporally, can be specifically illuminated on the sensor platform as metering ranges comprising a geometry, which varies temporally, and light emanating from these objects can be detected.

12. The analytical system according to claim 1, characterized in that the illuminating system encompasses one or a plurality of polychromatic or substantially monochromatic light sources.

13. The analytical system according to claim 12, characterized in that the one or plurality of polychromatic or substantially monochromatic light sources are chosen from the group of lasers "Vertical Well Surface emitting Lasers" VCSEL, edge-emitting laser diodes, superluminescent diodes SLD, light-emitting diodes LED, organic light-emitting diodes (OLED), gas discharge lamps and light bulbs.

14. The analytical system according to claim 1, characterized in that, before the illuminating light enters into the arrangement for the temporally variable spatial light modulation, the illuminating system in the optical light path comprises optical or electro-optical components for producing an intensity distribution of the illuminating light, which is homogenous across the illuminating cross section, wherein said components are preferably chosen from the group of optical projection systems, micro lens arrays, "light tunnels" or light rods".

15. The analytical system according to claim 1, characterized in that, before the illuminating light enters into the arrangement for the temporally variable spatial light modulation or in the further optical path in the direction of the sensor platform, the illuminating system comprises telecentrically acting optical components in the optical light path of the illuminating light.

16. The analytical system according to claim 1, characterized in that the optical system comprises provisions for corrections relating to the compensation of oblique light incidence according to Scheimpflug.

17. The analytical system according to claim 1, characterized in that the detection system comprises one or a plurality of detection units from the group of photodiodes, photomultipliers, avalanche diodes, CMOS arrays and CCD cameras.

18. The analytical system according to claim 1, characterized in that the detection system comprises one or a plurality of spectrally splitting electro-optical components for a selective detection of spectral characteristics of the light emanating from the metering ranges.

19. The analytical system according to claim 1, characterized in that the illuminating system and/or the detection system comprise components in the light path, which act in a polarization-selective manner.

20. The analytical system according to claim 19, characterized in that the components, which act in a polarization-selective manner, enable the differentiation between light, which is polarized in a transverse electric (TE) and transverse magnetic (TM) manner, which emanates from the metering ranges on the sensor platform.

21. The analytical system according to claim 1, characterized in that the index of refraction and/or the thickness of an adsorbing layer or the variations thereof in or on the metering ranges on the sensor platform can be determined from the signals of the one or the plurality of detectors and from the variations thereof.

22. The analytical system according to claim 4, characterized in that the effective index of refraction and/or the variations thereof in or on the metering ranges on the sensor platform can be determined from the signals of the one or the plurality of detectors and/or from the variations thereof.

23. The analytical system according to claim 22, characterized in that the angle of resonance for coupling illuminating light into a thin-film waveguide can be determined from the signals of the one or plurality of detectors and the variations thereof via a grid structured therein and/or variations of such an angle of resonance with reference to the surface normal of the sensor platform can be determined at a wavelength of the illuminating light, which is irradiated constantly.

24. The analytical system according to claim 22, characterized in that the resonance wavelength for coupling illuminating light into a thin-film waveguide can be determined from the signals of the one or plurality of detectors and the variations thereof via a grid structured therein and/or variations of such a resonance wavelength can be determined at a constant angle of irradiation of the illuminating light with reference to the surface normal of the sensor platform.

25. A method for generating and metering optical signals and/or the variations thereof from metering ranges, which are arranged in a one-dimensional or two-dimensional array on a substantially optically transparent sensor platform, using an analytical system according to one of the preceding claims, at least comprising an optical system comprising an illuminating system for illuminating metering ranges on the sensor platform comprising an arrangement identified as "SLM" for the temporally rapidly variable spatial light modulation as well as comprising a detection system comprising at least one detection unit for detecting signals from the metering ranges on the sensor platform in the direction of the transmission or reflection of the illuminating light in a spectral range, which comprises the spectral range of the illuminating light and a sensor platform, which can be inserted into the optical system, comprising metering ranges, which are arranged thereon in a one-dimensional or two-dimensional array, characterized in that in the operating state, illuminating patterns of a freely selectable and rapidly variable geometry, which can be determined by the settings of the SLM, can be generated on the sensor platform from an illuminating light, which enters into this SLM and which comprises a substantially homogenous intensity distribution in the cross section of the illuminating light at right angles to its direction of expansion.

26. The method according to claim 25, characterized in that a brightness distribution of the signals is metered by means of the detection system comprising at least one detection unit and that this brightness distribution is analyzed independent on the metered absolute signal intensities.

27. The method according to one of claims 25-26, characterized in that the optical signals and/or the variations thereof are generated from discrete metering ranges by means of one or a plurality of bonding or adsorption results between one or a plurality of analytes in one or a plurality of specimens and specific identification elements for said analytes in or on said metering ranges, wherein the specimens and the identification elements for the analytes on the metering ranges, which are to be detected in the specimens, are brought into contact with one another and in that a simultaneous qualitative and/or quantitative detection of a plurality of analytes in one or a plurality of specimens and/or of one or a plurality of analytes in a plurality of specimens is made possible from these optical signals and/or the variations thereof.

28. A method of using an analytical system, comprising:
using the system of claim 1 to:
determine chemical, biochemical or biological analytes in screening methods in pharmaceutical research, combinatory chemistry, clinical and preclinical development for quantitative and/or qualitative analyses,
determine kinetic parameters in affinity screening and in research for real time bonding studies,
make qualitative and quantitative analyte determinations, in particular for the DNA and RNA analysis and determining genomic or proteomic differences in a genome, such as, for example, individual nucleotide polymorphisms, metering protein-DNA interactions, for determining control mechanisms for the m-RNA expression and for the protein(bio)synthesis,
prepare toxicity studies as well as determining expression profiles, in particular for determining biological and chemical marker substances, such as mRNA, proteins, peptides or low-molecular organic (messenger) substances,
detect antibodies, antigens, pathogens or bacteria in pharmaceutical product research and development, in human and veterinary diagnostics, agrochemical product research and development, symptomatic and presymptomatic plant diagnostic,
stratify patients for pharmaceutical product development and for the therapeutic drug selection, or
detect pathogens, toxic substances and viruses, in particular of salmonella, prions, viruses and bacteria, in particular for analyzing food and the environment.

* * * * *